US011399706B2

(12) United States Patent
Ito et al.

(10) Patent No.: US 11,399,706 B2
(45) Date of Patent: Aug. 2, 2022

(54) ENDOSCOPE APPARATUS FOR SWITCHING BETWEEN ONE-SUBSTANCE OBSERVATION MODE AND TWO-SUBSTANCE OBSERVATION MODE BASED ON INPUT OF SELECTION OF DESIRED OBSERVATION MODE

(71) Applicant: OLYMPUS CORPORATION, Tokyo (JP)

(72) Inventors: Takeshi Ito, Hino (JP); Yoshihiko Watanabe, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 587 days.

(21) Appl. No.: 16/219,280

(22) Filed: Dec. 13, 2018

(65) Prior Publication Data
US 2019/0117055 A1    Apr. 25, 2019

Related U.S. Application Data

(63) Continuation of application No. PCT/JP2016/067702, filed on Jun. 14, 2016.

(51) Int. Cl.
*A61B 1/06*    (2006.01)
*A61B 1/04*    (2006.01)
(Continued)

(52) U.S. Cl.
CPC .......... *A61B 1/0676* (2013.01); *A61B 1/0005* (2013.01); *A61B 1/00009* (2013.01);
(Continued)

(58) Field of Classification Search
CPC ... A61B 1/0676; A61B 1/043; A61B 1/00186; A61B 1/0005; A61B 1/0684;
(Continued)

(56) References Cited

U.S. PATENT DOCUMENTS 4,974,076 A * 11/1990 Nakamura .............. A61B 1/05
348/71
7,658,710 B2 * 2/2010 Ueno .................. A61B 1/0646
600/160
(Continued)

FOREIGN PATENT DOCUMENTS

JP    2010-131265 A    6/2010
JP    2010131265 A *    6/2010
(Continued)

OTHER PUBLICATIONS

Japanese Office Action dated Apr. 28, 2020 in Japanese Patent Application No. 2018-523085.
(Continued)

*Primary Examiner* — John P Leubecker
(74) *Attorney, Agent, or Firm* — Scully, Scott, Murphy & Presser, P.C.

(57) ABSTRACT

An endoscope apparatus includes a scope including an imaging unit provided at a distal end of an insertion section to be inserted into an observation object, and a main body including a light source unit configured to emit illumination light that illuminates the observation object through the scope. The light source unit is configured to emit first narrow band light selected based on an absorption spectrum of a first characteristic substance, and second narrow band light selected based on an absorption spectrum of a second characteristic substance. The main body includes an image processing circuit configured to process image information acquired by the imaging unit. The endoscope apparatus also includes a display configured to display image information processed by the image processing circuit.

22 Claims, 17 Drawing Sheets

(51) Int. Cl.
  *A61B 1/00* (2006.01)
  *A61B 1/05* (2006.01)
  *A61B 1/07* (2006.01)
  *G02B 23/24* (2006.01)

(52) U.S. Cl.
  CPC ...... *A61B 1/00096* (2013.01); *A61B 1/00165* (2013.01); *A61B 1/00186* (2013.01); *A61B 1/043* (2013.01); *A61B 1/05* (2013.01); *A61B 1/0638* (2013.01); *A61B 1/0684* (2013.01); *A61B 1/07* (2013.01); *G02B 23/2461* (2013.01); *G02B 23/2469* (2013.01)

(58) Field of Classification Search
  CPC .............. A61B 1/0638; A61B 1/00009; A61B 1/00096; A61B 1/00165; A61B 1/05; A61B 1/07; G02B 23/2461; G02B 23/2469
  See application file for complete search history.

(56) References Cited

U.S. PATENT DOCUMENTS

| | | | |
|---|---|---|---|
| 2007/0016077 A1* | 1/2007 | Nakaoka | A61B 1/0005 600/476 |
| 2011/0237915 A1* | 9/2011 | Yamaguchi | A61B 5/14551 600/339 |
| 2012/0082446 A1* | 4/2012 | Kumai | A61B 1/05 396/164 |
| 2012/0130166 A1* | 5/2012 | Nishimura | A61B 1/0684 600/109 |
| 2012/0271103 A1* | 10/2012 | Gono | A61B 1/0684 600/109 |
| 2013/0006109 A1* | 1/2013 | Takei | A61B 1/00009 600/432 |
| 2013/0113911 A1* | 5/2013 | Hanano | G02B 23/2469 348/79 |
| 2015/0022647 A1* | 1/2015 | Takei | A61B 1/00186 348/70 |
| 2015/0087903 A1* | 3/2015 | Kuramoto | A61B 1/00006 600/109 |
| 2015/0094530 A1* | 4/2015 | Moriya | F21V 5/04 600/103 |
| 2015/0105614 A1* | 4/2015 | Igarashi | A61B 1/0646 600/104 |
| 2017/0112370 A1 | 4/2017 | Daidoji et al. | |

FOREIGN PATENT DOCUMENTS

| | | |
|---|---|---|
| JP | 2011167349 A | 9/2011 |
| JP | 2012-143349 A | 8/2012 |
| JP | 2014-50595 A | 3/2014 |
| JP | 2016-2133 A | 1/2016 |
| JP | 2016067780 A | 5/2016 |
| WO | 2012/140970 A1 | 10/2012 |
| WO | 2014/125724 A1 | 8/2014 |
| WO | 2015/145814 A1 | 10/2015 |
| WO | 2016/006371 A1 | 1/2016 |

OTHER PUBLICATIONS

International Search Report dated Aug. 16, 2016 received in PCT/JP2016/067702.

Japanese Office Action dated Sep. 8, 2020 received in Japanese Patent Application No. 2018-523085.

English translation of International Preliminary Report on Patentability dated Dec. 27, 2018 together with the Written Opinion received in related International Application No. PCT/JP2016/067702.

* cited by examiner

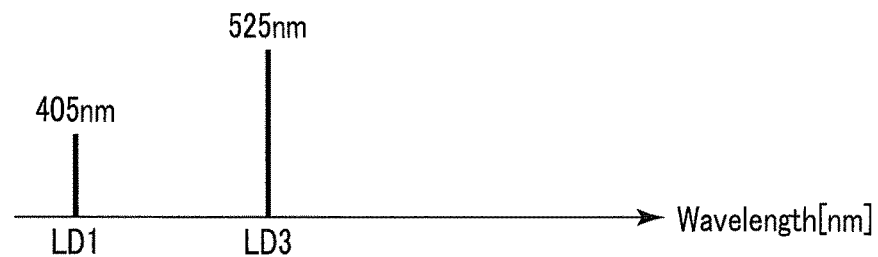
F I G. 4
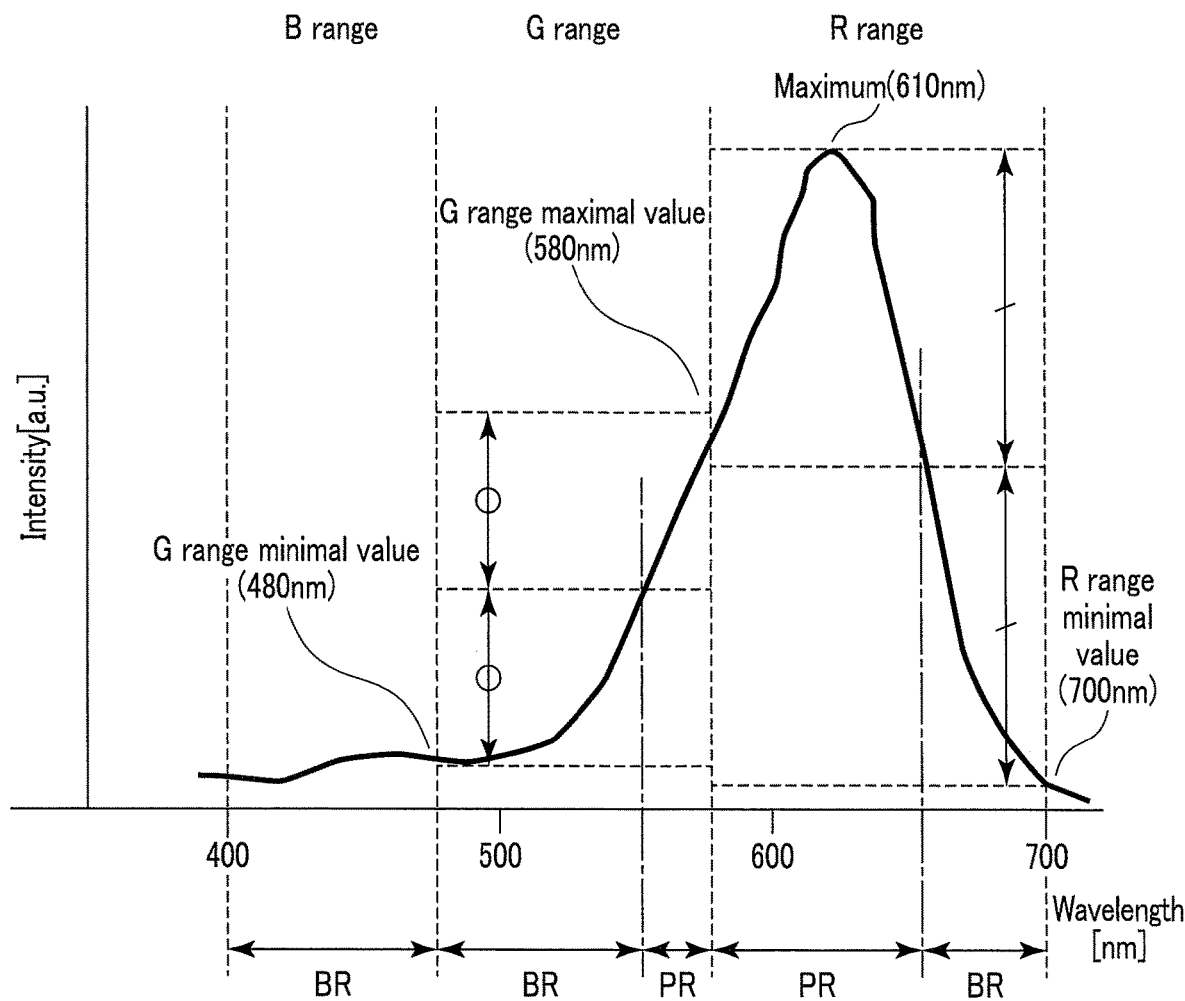
F I G. 5

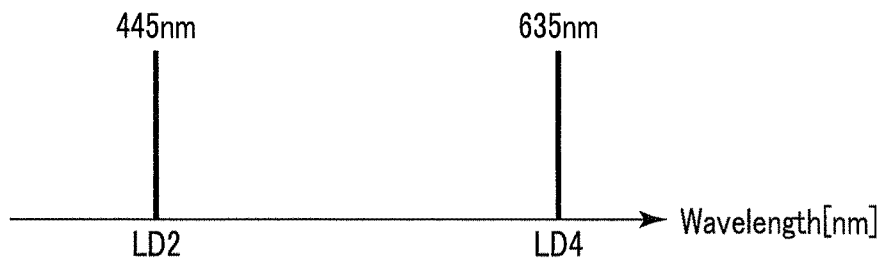

FIG. 10

| Type I | Round pit | Normal mucosa |
|---|---|---|
| Type II | Asteroid pit | |
| Type III$_S$ | Tubular or round pit that is smaller than the normal | Intra mucosal lesion (adenocarcinoma~M cancer) |
| Type III$_L$ | Tubular or round pit that is larger than the normal | |
| Type IV | Dendritic or gyrus-like pit | |
| Type V$_I$ | Irregular arrangement, amorphous structure | Invaded to submucosal layer (M~SM cancer) |
| Type V$_N$ | Loss or decrease of pits with irregular arrangement and amorphous structure | Deeply invaded into submucosal layer (beyond SM cancer) |

FIG. 11

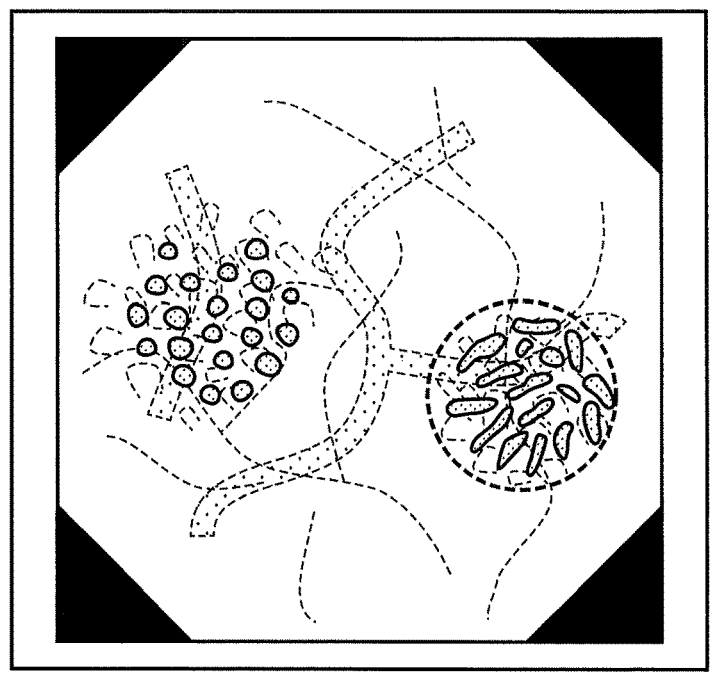
F I G. 13B
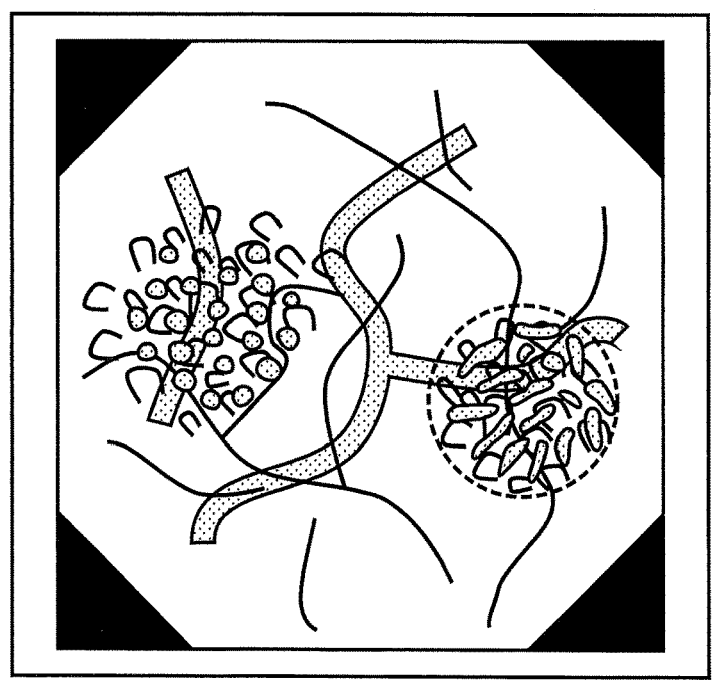
F I G. 13C

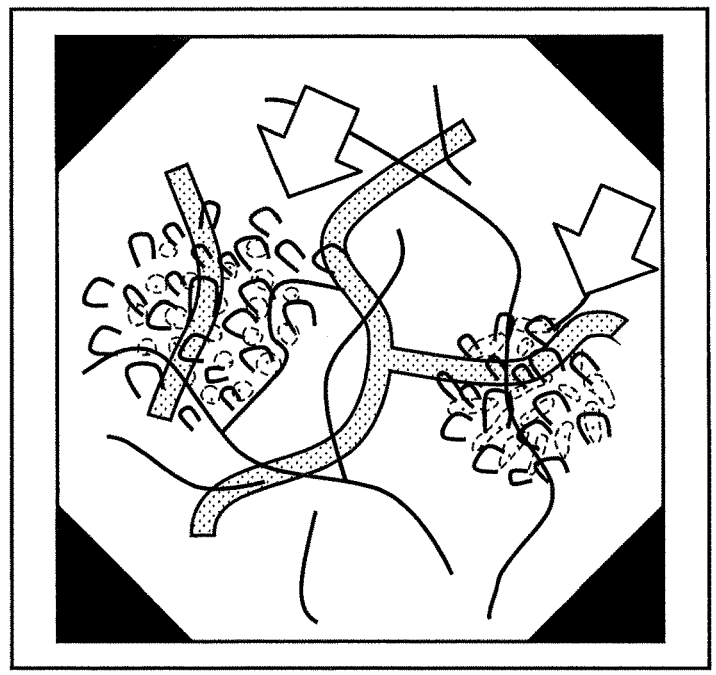
F I G. 13D
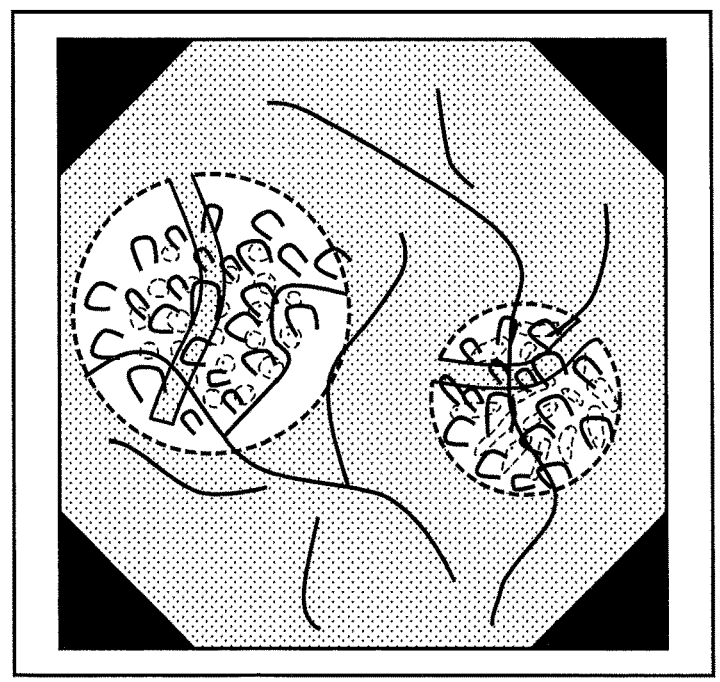
F I G. 13E

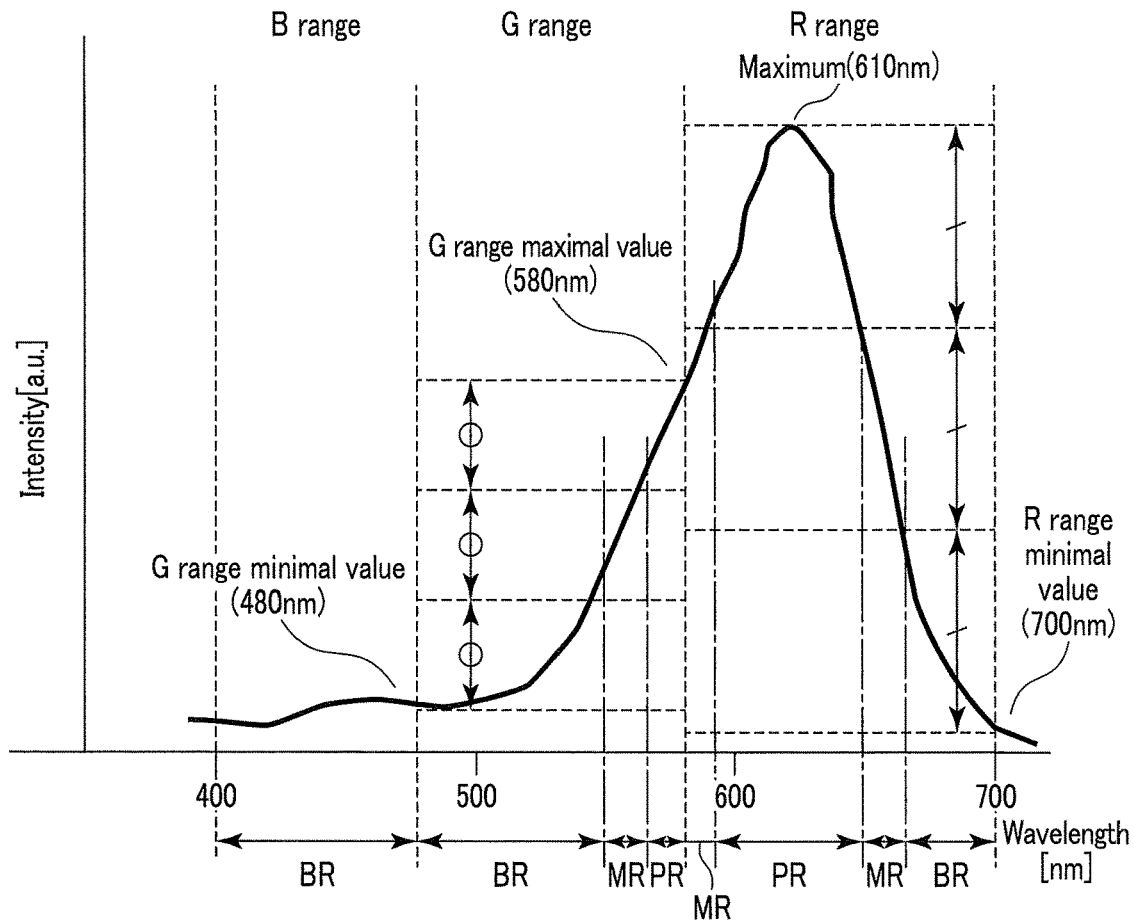
F I G. 15
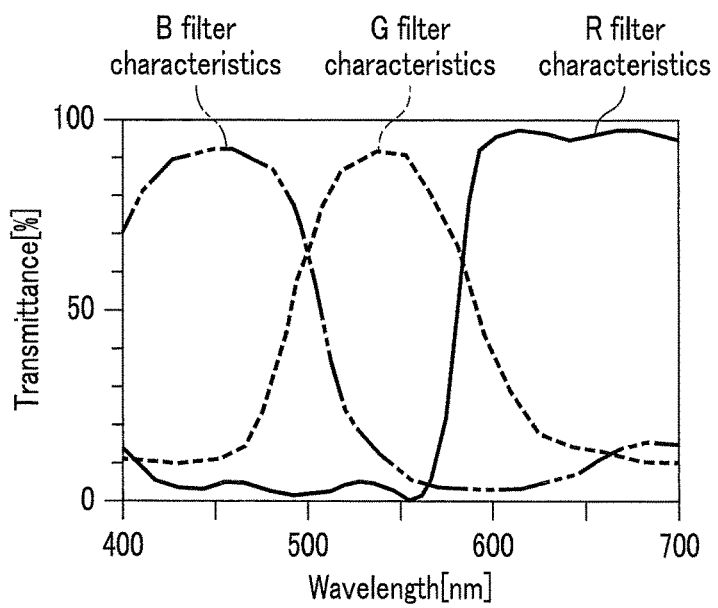
F I G. 16

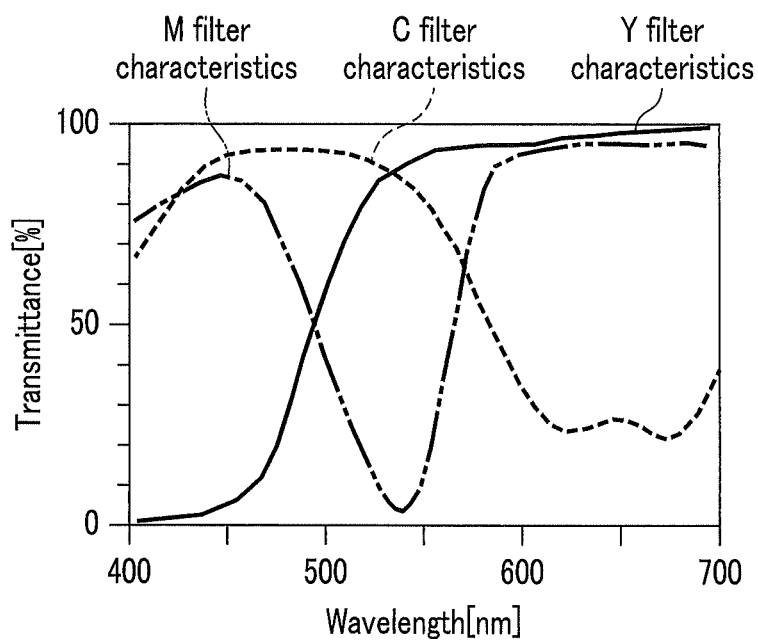
F I G. 17
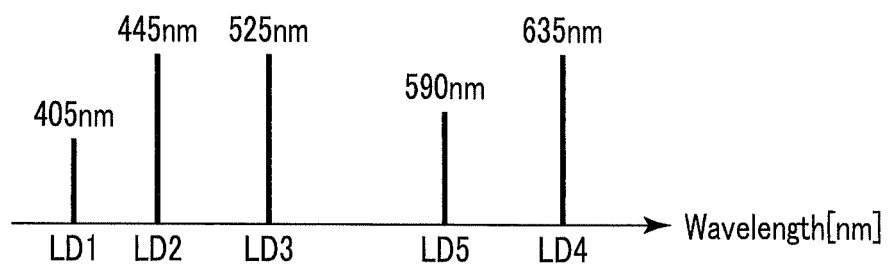
F I G. 18

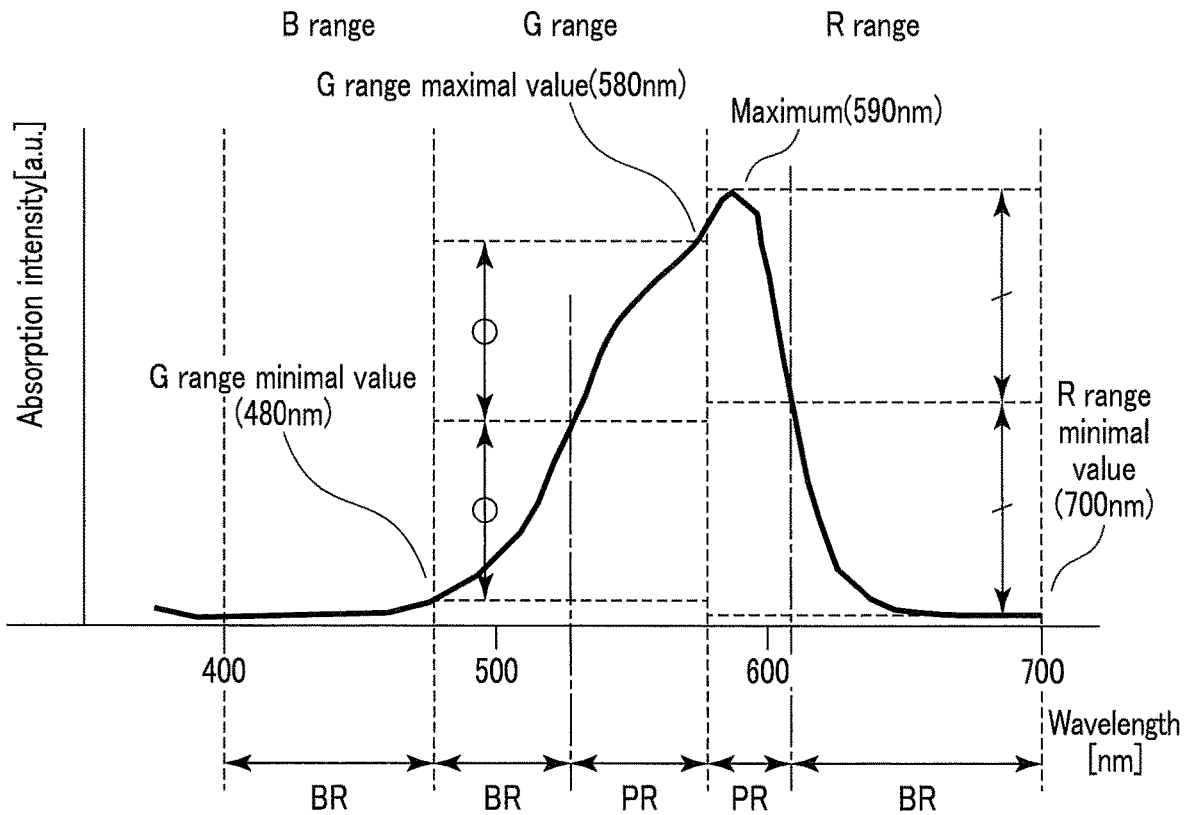
F I G. 19
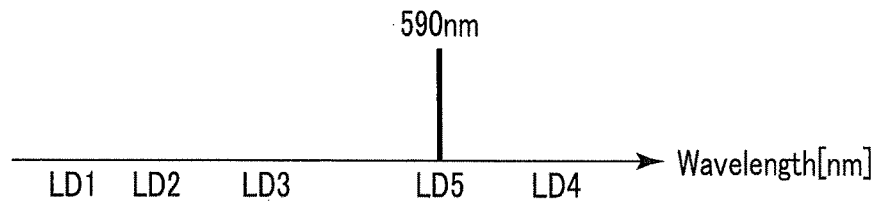
F I G. 20

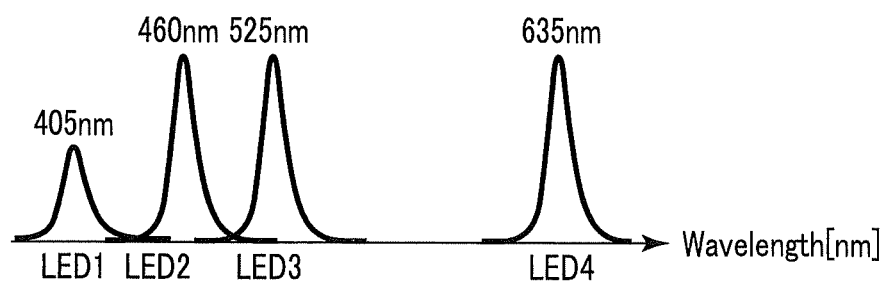
F I G. 25
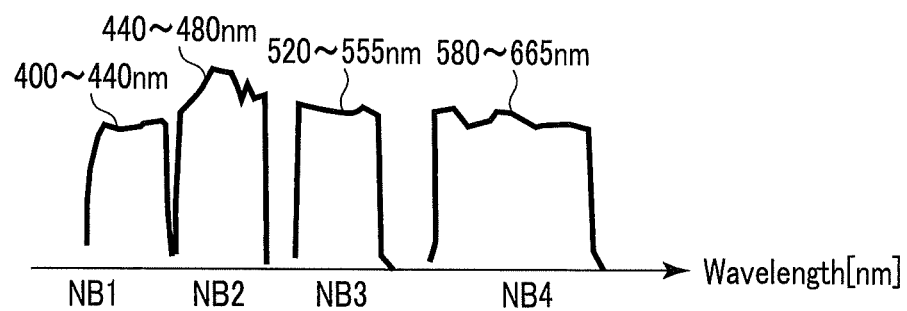
F I G. 26

ENDOSCOPE APPARATUS FOR SWITCHING BETWEEN ONE-SUBSTANCE OBSERVATION MODE AND TWO-SUBSTANCE OBSERVATION MODE BASED ON INPUT OF SELECTION OF DESIRED OBSERVATION MODE

CROSS-REFERENCE TO RELATED APPLICATIONS

This application is a Continuation Application of PCT Application No. PCT/JP2016/067702, filed Jun. 14, 2016, the entire contents of which are incorporated herein by reference.

BACKGROUND OF THE INVENTION

1. Field of the Invention

The present invention relates to an endoscope apparatus configured to acquire an image of an observation object.

2. Description of the Related Art

Jpn. Pat. Appln. KOKAI Publication No. 2014-50595 discloses an endoscope apparatus. This endoscope apparatus alternately irradiates a subject with oxygen saturation measurement light and blood vessel emphasis illumination light, and, while highlighting the superficial blood vessel and the intermediate blood vessel from an image of the obtained two frames, displays an image in which the color of the superficial blood vessel is changed only when an oxygen saturation level is low. As a result, an image in which a blood vessel course pattern is highlighted is displayed, and information for intuitively recognizing whether or not a part of the blood vessel course pattern is a lesion is displayed.

BRIEF SUMMARY OF THE INVENTION

An endoscope apparatus according to the present invention includes a scope. The scope includes: an insertion section to be inserted into an internal space of an observation object; an imaging unit provided at a distal end of the insertion section; and a control section configured to allow operating the insertion section. The endoscope apparatus also includes a main body. The main body includes: a light source unit configured to emit illumination light that illuminates the observation object through the scope, the light source unit including at least a first narrow band light source and a second narrow band light source, the light source unit being configured to emit at least two kinds of narrow band light of first narrow band light selected based on an absorption spectrum of a first characteristic substance, and second narrow band light selected based on an absorption spectrum of a second characteristic substance; an illumination controller configured to control operation of the light source unit; and an image processing circuit configured to process image information acquired by the imaging unit. The endoscope apparatus further includes a display configured to display the image information processed by the image processing circuit.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 shows a spectrum of illumination light when all laser light sources shown in FIG. 1 are turned on.

FIG. 4 shows a spectrum of illumination light in a one-substance observation mode (hemoglobin emphasis mode).

FIG. 5 shows an absorption spectrum of indigo carmine.

FIG. 10 shows an emission spectrum of the light source unit at a timing Tb1 shown in FIG. 8.

FIG. 11 is a diagram of pit pattern classification.

FIG. 13B shows an image in which indigo carmine is emphasized, corresponding to FIG. 12B.

FIG. 13C shows an image in which both blood vessels and indigo carmine are emphasized, corresponding to FIG. 12C.

FIG. 13D shows an image in which the visibility of a characteristic substance region is enhanced in the image of FIG. 13A by an arrow.

FIG. 13E shows an image in which the visibility is enhanced by lowering the brightness of a peripheral range of the characteristic substance region in the image of FIG. 13A.

FIG. 15 shows absorption peak ranges PR, absorption bottom ranges BR, and absorption intermediate ranges MR defined according to a modification of the first embodiment with respect to the absorption spectrum of indigo carmine.

FIG. 16 shows an example of a spectrum of a light transmittance of a primary color filter used for an image sensor.

FIG. 17 shows an example of a spectrum of a light transmittance of a complementary color filter used for the image sensor.

FIG. 18 shows a spectrum of light that can be emitted by the light source unit in a second embodiment.

FIG. 19 shows an absorption spectrum of crystal violet.

FIG. 20 shows a spectrum of illumination light in a one-substance observation mode (crystal violet emphasis mode).

FIG. 25 shows a spectrum of light emitted from the light source unit, in which the laser light source of the first embodiment is replaced by a LED light source.

FIG. 26 shows spectra of narrow band light produced by a combination of an Xe lamp and a filter.

DETAILED DESCRIPTION OF THE INVENTION

Hereinafter, an endoscope apparatus according to an embodiment of the present invention will be described with reference to the drawings. In the present specification, the endoscope apparatus is not limited to a medical endoscope apparatus used for examining a living body, or an industrial endoscope apparatus used for observing industrial products and other various products or for observing inside a lumen existing in various places, and generally refers to a device including an insertion section configured to be inserted into a lumen, such as a body cavity, etc., of an observation object, and observe the inner surface of the lumen.

First Embodiment

Hereinafter, a first embodiment of the present invention will be described by an example of a medical endoscope apparatus, particularly, a digestive endoscopy apparatus.

[Configuration]

Figure 1:
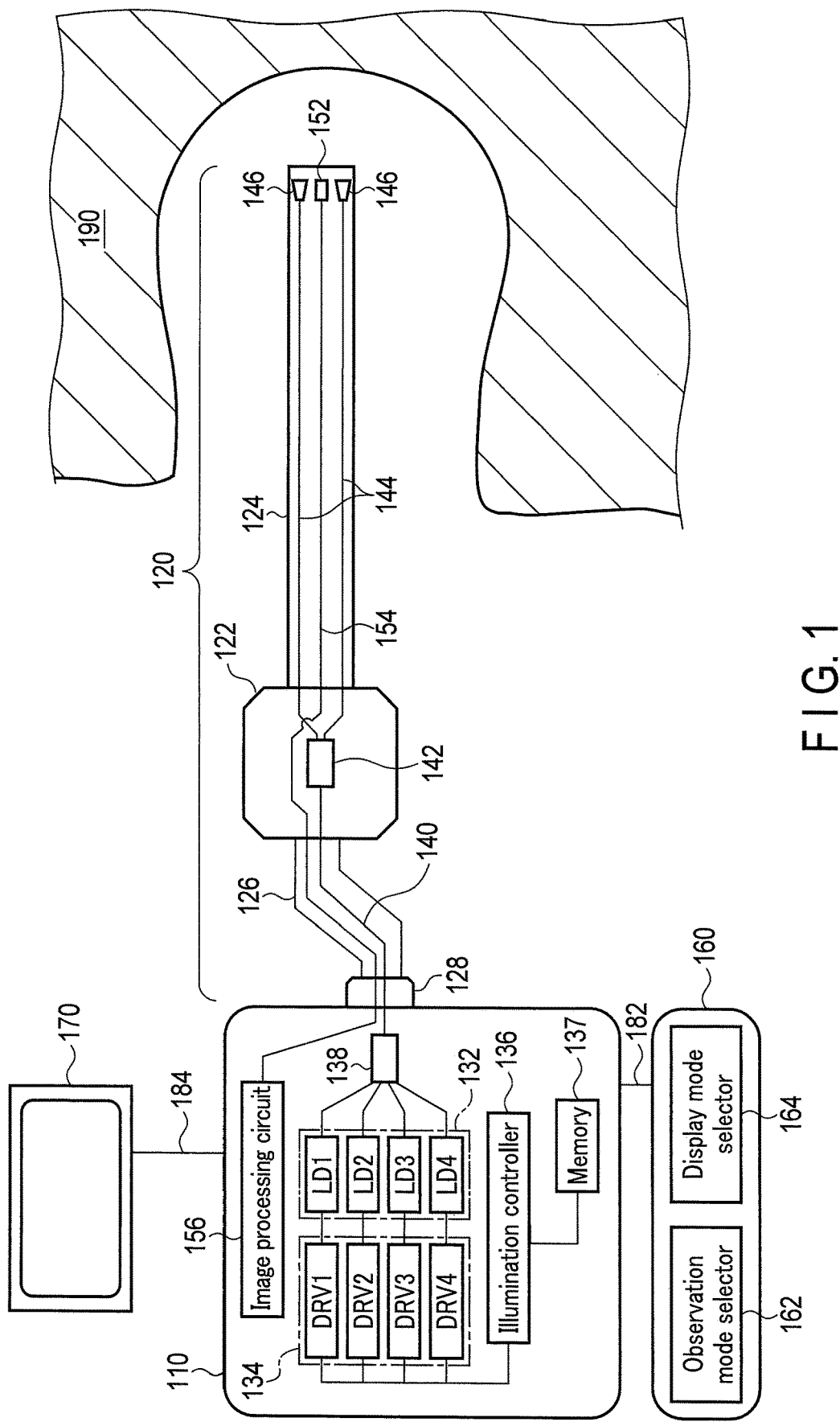
FIG. 1 is a block diagram of an endoscope apparatus according to a first embodiment of the present invention.

FIG. 1 is a block diagram of an endoscope apparatus according to a first embodiment of the present invention. The endoscope apparatus according to the present embodiment is configured by a main body 110, a scope 120, an input device 160, and a display 170. First, each configuration of the endoscope apparatus according to the present embodiment will be described.

[Scope 120]

The scope 120 is configured by an insertion section 124 having flexibility so as to be inserted into an internal space of an observation object 190, such as a body cavity, a control section 122 for an operator, such as a doctor, to hold and control the insertion section 124 for an observation operation, a flexible connecting cable 126 for connecting the main body 110 and the scope 120, a connector 128 to allow attachment and detachment with respect to the main body 110, etc.

At the distal end of the insertion section 124, two illuminating units 146 configured to emit illumination light toward the observation object 190, and an imaging unit 152 configured to receive the illumination light reflected or scattered on the surface of the observation object 190 to acquire an image, are arranged.

A light guide path is provided in the scope 120, and guides laser light emitted from the light source unit 132 provided in the main body 110 to the illuminating unit 146 provided at the distal end of the insertion section 124. The light guide path is configured by, from the connector 128 side, one first optical fiber 140 provided in the connecting cable 126, a 1-input 2-output light branching optical element 142 (1×2 light branching optical element) provided in the control section 122, and two second optical fibers 144 provided in the insertion section 124. The laser light emitted from the light source unit 132 provided in the main body 110 enters the scope 120 through the connector 128, and then enters the two illuminating units 146 through the first optical fiber 140, the light branching optical element 142, and the two second optical fibers 144. The light branching optical element 142 has a function of distributing light entering from one input end to two output ends, in a manner that the light quantity of each wavelength is substantially equally distributed. In other words, each of the two second optical fibers 144 provided in the insertion section 124 guides the laser light from the light source unit 132 that has been divided into the substantially equal light quantity for each wavelength to the two illuminating units 146.

The two illuminating units 146 have substantially equal light conversion functions to each other. The present embodiment has a function of broadening the radiation angle and shortening the coherence length without converting the wavelength of the laser light. Such function can be achieved by a diffusion plate or a member including diffusion particles, an optical element such as a lens, or a combination thereof. Thereby, the illuminating unit 146 emits light having a wide radiation angle and low coherence as illumination light without changing the wavelength of the laser light emitted from the light source unit 132.

The imaging unit 152 provided at the distal end of the insertion section 124 of the scope 120 includes an imaging optical system and an image sensor. The image sensor according to the present embodiment is, for example, a CMOS type image sensor, in which a general Bayer array RGB color filter is mounted. That is, the image sensor is a primary color filter type image sensor having a color filter configured to separately acquire light of three color ranges of an R range, a G range, and a B range. In other words, the primary color filter type image sensor includes an R pixel being a color pixel configured to separately acquire the light of the R range, a G pixel being a color pixel configured to separately acquire the light of the G range, and a B pixel being a color pixel configured to separately acquire the light of the B range. In this case, the imaging unit 152 itself configures an imaging system configured to separately acquire each of an R image, a G image, and a B image.

Furthermore, an image signal line 154 is provided in the scope 120. The image signal line 154 transmits the image information of the observation object 190 acquired by the imaging unit 152 provided at the distal end of the insertion section 124 to the main body 110. The image signal line 154 extends through the insertion section 124, the control section 122, and the connecting cable 126, and is connected to the main body 110 through the connector 128. The image signal line 154 may be anything as long as it can transmit an image signal, and it can be configured by, for example, an electrical wire or an optical fiber for optical communication. Although the image signal line 154 is drawn to be configured by one signal line in FIG. 1, it may be configured by signal lines in accordance with the amount of the image signal desired to be transmitted, or the required transmission speed, etc.

Mounted on the insertion section 124 of the present embodiment, in addition to a bending mechanism for bending the distal end is, a forceps hole into which a forceps, etc., can be inserted to perform various treatments, and air/water supply pipes that can blowout or suction liquids and gases, and functions and mechanisms that are mounted on general endoscope devices. However, they are not shown in FIG. 1 for the sake of simplicity.

[Main Body 110]

The main body 110 includes the light source unit 132 configured to emit plural kinds of narrow band light, and a driver 134 configured to drive the light source unit 132. The light source unit 132 includes laser light sources LD1, LD2, LD3, and LD4 configured to emit laser light. The driver 134 includes drive circuits DRV1 to DRV4 configured to respectively drive the laser light sources LD1 to LD4.

Each of the laser light sources LD1 to LD4 is a semiconductor light source, for example, a narrow band semiconductor light source configured to directly emit desired narrow band light. The narrow band semiconductor light source is, for example, a semiconductor laser light source configured to emit laser light.

The main body 110 also includes an illumination controller 136 configured to control the quantities of light emitted from the laser light sources LD1 to LD4 through the drive circuits DRV1 to DRV4, and the light emission timing thereof, etc., an image processing circuit 156 configured to apply necessary image processing to the image signal acquired by the imaging unit 152, and a memory 137 configured to store illumination light control information and/or image processing information. The illumination light control information includes, for example, a wavelength, a light quantity ratio of each wavelength, and a light emission timing of the laser light emitted in each observation mode described later on. The image processing information includes, for example, image parameters set in advance for each observation mode described later on.

Each of the laser light sources LD1 to LD4 used in the present embodiment includes a semiconductor laser element and a temperature stabilizing section configured to control the temperature of the semiconductor laser element. The characteristics of the laser light sources LD1 to LD4 are as follows.

The laser light source LD1 is configured to emit blue-violet laser light having a wavelength of 405 nm. The output is approximately 1.5 W.

The laser light source LD2 is configured to emit blue laser light having a wavelength of 445 nm. The output is approximately 3 W.

The laser light source LD3 is configured to emit green laser light having a wavelength of 525 nm. The output is approximately 3 W.

The laser light source LD4 is configured to emit red laser light having a wavelength of 635 nm. The output is approximately 3 W.

The drive circuits DRV1 to DRV4 are electrically connected to the corresponding laser light sources LD1 to LD4, respectively. That is, as shown in FIG. 1, the drive circuit DRV1 is electrically connected to the laser light source LD1, the drive circuit DRV2 is electrically connected to the laser light source LD2, the drive circuit DRV3 is electrically connected to the laser light source LD3, and the drive circuit DRV4 is electrically connected to the laser light source LD4, respectively. Each of the laser light sources LD1 to LD4 oscillates the laser light by currents from the drive circuits DRV1 to DRV4.

All of the drive circuits DRV1 to DRV4 are electrically connected to the illumination controller 136. The illumination controller 136 is configured to control the light quantity and the light emission timing, etc., of the laser light emitted from the laser light sources LD1 to LD4 by transmitting control signals such as the light quantity and the light emission timing of the laser light to each of the drive circuits DRV1 to DRV4. As a result, the laser light sources LD1 to LD4 are able to emit the laser light with the light quantity and the light emission timing of the laser light independently of each other. That is, it is possible to independently oscillate or flicker each of the laser light sources LD1 to LD4 on the basis of an observation mode and/or a display mode, etc. described later on.

The laser light emitted from the laser light sources LD1 to LD4 enters the input end of a light combiner 138. The light combiner 138 in the present embodiment is a 4-input 1-output, that is, a 4×1 light combiner.

Figure 2:
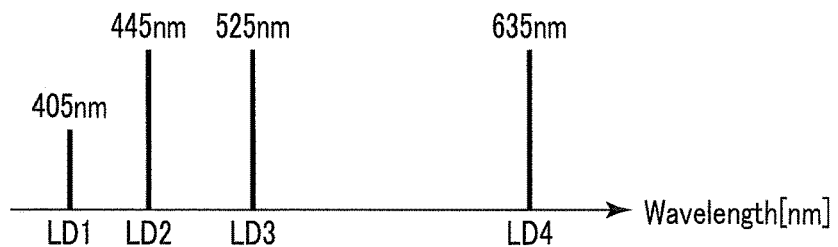

The laser light emitted from the laser light sources LD1 to LD4 enters the input end of the light combiner 138 through an optical fiber connected to each of the laser light sources LD1 to LD4, and an internal connector, not shown. That is, the laser light sources LD1 to LD4 are optically connected to each of the four input ends of the light combiner 138. Four colors of the laser light that have entered the light combiner 138 are combined in the light combiner 138 and then emitted from one output end. The one output end of the light combiner 138 is optically connected to the first optical fiber 140 through the connector 128. That is, the four colors of the laser light emitted from the laser light sources LD1 to LD4 are combined and then enter the first optical fiber 140. The four-color laser light that has entered the first optical fiber 140 is guided to the illuminating units 146 through the light branching optical element 142 and the second optical fibers 144, then converted into illumination light with a wide radiation angle and low coherence as described above, and then radiated toward the observation object 190. An example of the spectrum of this illumination light is shown in FIG. 2.

The drive circuits DRV1 to DRV4 are electrically connected to the semiconductor laser elements of the laser light sources LD1 to LD4, and configured to supply a desired current to the semiconductor laser elements to cause laser oscillation of the semiconductor laser elements. In order to stabilize the quantity of laser light oscillated from the semiconductor laser element, a laser light quantity monitor (not shown) is provided in the main body 110. In accordance with an output value of the laser light quantity monitor, the drive circuits DRV1 to DRV4 adjust the amount of current to be supplied to the semiconductor laser element so as to obtain a desired laser light quantity. In adjustment of the laser light quantity, in addition to the method using the light quantity monitor, it is also preferable to use a method of storing a table of the current and the light quantity in advance and adjusting the supply current with reference to this table, or various other methods that are known.

Furthermore, the drive circuits DRV1 to DRV4 output control signals for controlling the temperature stabilizing section configured to control the temperature of the semiconductor laser elements of the laser light sources LD1 to LD4. It is generally known that, when the temperature of the semiconductor laser element changes, the light quantity and the wavelength of the oscillating laser light change. For this reason, in the present embodiment, the temperature stabilizing section is provided in order to obtain a stable light quantity and a stable wavelength of the laser light. The temperature stabilizing section can be configured by, for example, a Peltier element thermally connected to the semiconductor laser element. Each of the drive circuits DRV1 to DRV4 control the Peltier element and supply a control signal and power so that the semiconductor laser element has an appropriate temperature of, for example, 25° C. As a method of stabilizing the temperature of the semiconductor laser element, in addition to the method using a Peltier element, various methods such as a method using a heat sink of a sufficient heat capacity, and a method using a forced air cooling, etc., are known, which are also preferable to be used. Furthermore, a method in which the temperature of the semiconductor laser element is measured by a temperature sensor, and the amount of current to be supplied to the semiconductor laser element is adjusted based on the measured temperature can be used. The temperature stabilizing mechanism can be independently combined with each of the four laser light sources LD1 to LD4, or laser light sources LD1 to LD4 can be combined with one temperature stabilizing mechanism.

The illumination controller 136 is electrically connected to the drive circuits DRV1 to DRV4 and is configured to control the light quantity independently or in conjunction with the laser light sources LD1 to LD4 through the drive circuits DRV1 to DRV4. The emission timing of each laser light in this embodiment will be described later.

The image processing circuit 156 is configured to perform image processing to convert an image signal obtained by the imaging unit 152 and transmitted by the image signal line 154 into a signal displayable by a display 170. In the image processing, image processing suitable for the illumination light selected according to the observation mode and the display mode described later on is performed, which allows the operator to display desired image information on the display 170 and confirm the image information. Therefore, the illumination controller 136 and the image processing circuit 156 are connected by an electrical wire (not shown), and the image processing circuit 156 is configured to obtain the information on the light emission timing and the light quantity of the illumination light as necessary, and apply the processing to the image signal in accordance with the information.

The connector 128 has a function of detachably connecting the scope 120 and the main body 110. The connector 128 has a function of attaching the image signal line 154 to transmit the image signal, the optical fiber 140 to guide the laser light, a power line (not shown) to supply power to the imaging unit 152, and the electrical wire and/or the optical wiring necessary for the endoscope apparatus to function, in an electrically and/or optically detachable manner. The connector 128 further has a function of detachably attaching a tube pipe, etc., for feeding a gas and a liquid, etc., necessary for the operation of the endoscope apparatus.

In the present embodiment, an example of each of the laser light sources LD1 to LD4 including one semiconductor laser element is shown; however, the present embodiment is not limited thereto. It is also preferable to treat a combination of semiconductor laser elements having substantially the same wavelength as one laser light source LD1 to LD4. In this case, it is also possible to provide a light combiner (not shown) in the laser light sources LD1 to LD4 so that laser light from semiconductor laser elements is outputted from one exit end, or to increase the input end of the light combiner 138 of FIG. 1 in accordance with the number of semiconductor laser elements. For example, in the case where the laser light source LD3 configured to emit green light is configured by a combination of three 1 W output semiconductor laser elements, the light combiner 138 in FIG. 1 may be a 6×1 optical combiner with 6 inputs and 1 output, in which three of six input ends are optically connected to the semiconductor laser elements configured to emit the green light of the laser light source LD3.

By mounting semiconductor laser elements on one of the laser light source LD1 to LD4, for example, a sufficient quantity of light can be obtained even when a semiconductor laser element of a desired wavelength cannot procure light with a sufficient quantity. Moreover, by combining low-cost, low-powered lasers, cost reductions can be achieved. On the other hand, by using one semiconductor laser element for each of the laser light source LD1 to LD4, the size of the main body 110 can be reduced, allowing the control system to be simplified, and power consumption to be reduced.

The illumination controller 136 and/or the image processing circuit 156 may be configured by, for example, a hardware circuit including an ASIC and the like. Alternatively, The illumination controller 136 and/or the image processing circuit 156 may be configured from a processor and a memory to which the processor is accessible. In this case, the memory stores in advance a program code that causes the processor to function as the illumination controller 136 and/or the image processing circuit 156.

[Display 170]

The display 170 is configured to display an image of the observation object 190 that is acquired by the imaging unit 152 mounted on the scope 120, and subjected to image processing by the image processing circuit 156 mounted on the main body 110. The display 170 can be configured by various kinds of commonly used display devices, such as a liquid crystal monitor.

The display 170 and the main body 110 are electrically connected by an electrical wire 184. Image information, which is obtained by processing by the image processing circuit 156 in the main body 110 an image signal acquired by the imaging unit 152 of the scope 120 and then transmitted through the image signal line 154, is transmitted to the display 170 by the electrical wire 184. The display 170 displays this image information for the operator.

In FIG. 1, the electrical wire 184 connecting the display 170 and the main body 110 is drawn as being configured by one signal line; however, the number is not limited thereto. The electrical wire 184 may be configured by two or more electrical wires as necessary. In FIG. 1, the illustration of an electrical wire to supply electric power necessary for the operation of the display 170 is omitted for simplicity.

In the present embodiment, an example of transmitting image information through the electrical wire 184 provided between the display 170 and the main body 110 is given; however, the transmission is not limited thereto. Various signal transmission techniques that are usually used, such as wireless communication and optical communication, can be used.

[Input Device 160] The input device 160 is used for selecting and switching observation modes and/or display modes described later on. The input device 160 includes an observation mode selector 162 configured to select an observation mode and a display mode selector 164 configured to select a display mode. In the case where an operator, for example, a doctor, who observes the observation object 190 wishes to change the start of observation, or change the current observation mode or display mode, the input device 160 is operated to set or select the observation mode and/or the display mode. Information on the observation mode input from the observation mode selector 162 is transmitted to the illumination controller 136 and the image processing circuit 156. Information on the display mode input from the display mode selector 164 is transmitted to the image processing circuit 156.

In the present embodiment, an observation mode and a display mode that are most frequently used are automatically selected as the default. For example, a white observation mode using white light is selected as the observation mode in default, and a standard display mode displaying only a white observation image and general information such as a date and time and a patient name is selected as the display mode in default. The observation mode and the display mode will be described later on.

The input device 160 can be configured by various commonly used input devices. In the present embodiment, an ordinary keyboard or a touch panel type input device is used. The input device 160 is connected to the main body 110 by the electrical wire 182. Input information from the input device 160, that is, information on the observation mode and/or the display mode, is transmitted to the main body 110 through the electrical wire 182. The input information transmitted to the main body 110 is transmitted to the illumination controller 136 and/or the image processing circuit 156 by a signal line (not shown). The illumination controller 136 controls the light quantity and light emission timing of the laser light sources LD1 to LD4 based on the received input information. Furthermore, the image processing circuit 156 processes the image signal from the imaging unit 152 based on the received input information and then transmits the processed image signal to the display 170.

In the present embodiment, the input device 160 is assumed to be configured by an independent unit; however, it is not limited thereto. For example, it is also possible to incorporate the input device 160 into the control section 122 of the scope 120. In this case, the input information is transmitted to the main body 110 through the connecting cable 126 and the connector 128. The input device 160 can also be provided in the display 170. In such case, all of the input device 160 can be provided in the display 170 and the control section 122, or a part of the input device 160 can be provided in the display 170 or the control section 122.

Furthermore, an example of connecting the input device 160 and the main body 110 by the electrical wire 182 is given; however, the connection is not limited thereto. The input device 160 and the main body 110 can be connected by an optical wiring, etc., or can be connected by a wireless connection by ordinary radio waves or infrared rays.

[Operation]

The basic operation of the endoscope apparatus according to the present embodiment will be described.

First, the operator turns on the power. When the power is turned on, in the same manner as a usual endoscope apparatus, a self-check circuit, etc. confirms whether or not the apparatus is operating normally. When it is confirmed to operate normally, a predetermined current is supplied from the drive circuits DRV1 to DRV4 to the laser light sources LD1 to LD4, and an operation to warm the laser light sources LD1 to LD4 for stabilization is performed.

The operator takes out the scope 120 stored separately from the main body 110, and connects the connector 128 of the scope 120 to the main body 110. In the same manner as with a usual endoscope apparatus, the main body 110 confirms the type of the connected scope, etc., and confirms the observation mode, etc. that can be realized by the combination of the main body 110 and the scope 120.

When the connection of the scope 120 is confirmed, the illumination controller 136 provided in the main body 110 transmits control signals to the drive circuits DRV1 to DRV4 so as to turn on at least one of the laser light sources LD1 to LD4 with an observable light quantity. Here, which of the laser light sources LD1 to LD4 is to be turned on is determined for each preset observation mode (described later). Information on which of the laser light sources LD1 to LD4 is to be turned on in which observation mode, which observation mode is the default observation mode, etc., is stored in the memory 137 provided in the main body 110. Generally, since the white observation mode is set as a default, the illumination controller 136 transmits control signals to the drive circuits DRV1 to DRV4 so as to cause the laser light sources LD1 to LD4 to emit light having a wavelength and a light quantity ratio for the white observation mode. In the case where the operator inputs a desired observation mode from the input device 160, the illumination controller 136 transmits control signals to the drive circuits DRV1 to DRV4 so that the laser light sources LD1 to LD4 corresponding to the observation mode input by the operator are turned on with the light quantity corresponding to the observation mode regardless of the default setting.

The drive circuits DRV1 to DRV4 control the corresponding laser light sources LD1 to LD4 by supplying drive currents to the laser light sources LD1 to LD4 so as to cause the laser light sources LD1 to LD4 to emit light with the light quantity and timing according to the control signal from the illumination controller 136, respectively. At this time, the drive circuits DRV1 to DRV4 control the laser light sources LD1 to LD4 by referring to information on the relationship between the drive current of each of the laser light sources LD1 to LD4 and the quantity of emitted light stored in the memory 137 provided in the main body 110, or information of such as the basic characteristics and individual differences of the laser light sources LD1 to LD4 such as the relationship between the drive current and the oscillation wavelength. From the illumination controller 136, the control signals of the laser light sources LD1 to LD4 are sequentially transmitted to the drive circuits DRV1 to DRV4. The drive circuits DRV1 to DRV4 control the laser light sources LD1 to LD4 to synchronize with each other and to emit light at a desired timing and light quantity while referring to a timing circuit, etc. (not shown) in the main body 110.

The laser light sources LD1 to LD4 perform laser oscillation according to the drive currents supplied from the drive circuits DRV1 to DRV4, and emit laser light having a predetermined wavelength. The laser light sources LD1 to LD4 control the temperature thereof to a desired value by the temperature stabilizing section (not shown) such as a Peltier device. This allows the laser light sources LD1 to LD4 to emit light at a stable temperature regardless of the ambient temperature, and allows the wavelength of the laser light and the light quantity with respect to the drive current to be stabilized.

The laser light emitted from the laser light sources LD1 to LD4 enters each input end of the light combiner 138 connected to each of the laser light sources LD1 to LD4, and travels toward a combiner of the light combiner 138. The laser light emitted from the laser light sources LD1 to LD4 are combined by the light combiner 138 and enter the first optical fiber 140, which is configured by one optical fiber. The laser light that has entered the first optical fiber 140 enters the scope 120 through the connector 128 and reaches the light branching optical element 142 arranged in the control section 122. The light branching optical element 142 distributes the light that has entered from one input end at 1:1 regardless of the wavelength, and causes it to enter the two second optical fibers 144. That is, the laser light emitted from the laser light sources LD1 to LD4 are branched so that the light quantity ratio in each wavelength is 1:1, and then enter the two second optical fibers 144.

The laser light from the laser light sources LD1 to LD4 that have entered each of the two second optical fibers 144 are guided to the two illuminating units 146 provided at the distal end of the insertion section 124 of the scope 120. Since the two illuminating units 146 have substantially equal light conversion characteristics, and the laser light guided by the two second optical fibers 144 are light with substantially equal spectrum and light quantity, as a result, the illumination light emitted from the two illuminating units 146 are substantially equal in brightness, spectrum, light distribution, and coherence length, etc.

A part of the illumination light emitted from the two illuminating units 146 is reflected or scattered on the surface of the observation object 190, and a part thereof is reflected or scattered while traveling inside the observation object 190. Apart of the reflected or scattered light enters the imaging unit 152 provided at the distal end of the insertion section 124 of the scope 120. That is, the imaging unit 152 images an image of the inner surface of the observation object 190 that is illuminated by the illumination light emitted from the illuminating unit 146.

The imaging unit 152 includes an image sensor including a Bayer array RGB color filter. The image of the inner surface of the imaged observation object 190 is converted into an electric signal by the image sensor and then transmitted to the image processing circuit 156 in the main body 110 through the image signal line 154 provided in the scope 120.

The image processing circuit 156 receives the image signal acquired by the imaging unit 152 and then transmitted through the image signal line 154, and performs appropriate image processing. The image processing may be different depending on an observation mode and/or a display mode described later on. The image processing circuit 156 performs appropriate image processing based on the observation mode and/or display mode set by default, or based on the observation mode and/or display mode inputted by an operator from the input device 160. The relationship between the observation mode and/or the display mode and the image processing to be performed is stored in the memory 137 provided in the main body 110.

The memory 137 may be provided in the image processing circuit 156. In addition, the memory 137 may be provided in the scope 120 instead of being provided in the main body 110.

Furthermore, the image processing circuit 156 may adjust the image processing based on the light emission pattern from each of the laser light sources LD1 to LD4 controlled by the illumination controller 136, that is, the wavelength information, the light quantity ratio between wavelengths, and the light emission timing, etc. Information on what kind of image processing is to be performed in what kind of light emission pattern is stored in the memory 137 provided in the main body 110.

The image information processed by the image processing circuit 156 is transmitted to the display 170 through the electrical wire 184. The display 170 displays the transmitted image information. The display 170 also displays information on the observation mode and/or the display mode input from the input device 160. Furthermore, the display 170 can display various information such as the information on the observation object 190, the observation date and time, and the time required for observation. These pieces of information include information stored in the memory 137 provided in the main body 110, information on a clock and a timer, and information input from the input device 160, etc.

The operator inserts the insertion section 124 into the observation object 190 while operating the insertion section 124 and the control section 122 of the scope 120, and observes the image of the inner surface of the observation object 190 displayed on the display 170. During observation and before and after observation, the operator inputs information from the input device 160 as needed or selects the observation mode and/or the display mode. In conjunction with the input information by the operator, the endoscope apparatus appropriately performs the above-described processing and supports the observation operation of the operator.

[Mode Select]

The endoscope apparatus according to the present embodiment is capable of performing observation in observation modes, and is capable of performing display in display modes. Hereinafter, each of the observation mode and the display mode will be described in detail in order.

<Observation Mode>

The endoscope apparatus according to the present embodiment is capable of performing observation in characteristic substance observation modes that can observe the characteristic substance that may be present in the observation object 190 with a good contrast, in addition to observation under the normal white observation mode. The characteristic substance observation mode of the present embodiment has four characteristic substance observation modes of a one-substance observation mode (hemoglobin emphasis mode), a one-substance observation mode (Indigo Carmine emphasis mode), a two-substance observation mode (hemoglobin-indigo carmine emphasis mode), and an illumination light sequential radiation mode. The one-substance observation mode and the two-substance observation mode are modes capable of observing the characteristic substance with a better contrast than the white observation mode. That is, the endoscope apparatus according to the present embodiment can perform observation in five observation modes.

The observation mode is selectable by inputting information from the observation mode selector 162 of the input device 160. Information on the observation mode input from the observation mode selector 162 is transmitted to the illumination controller 136 and the image processing circuit 156. The illumination controller 136 and/or the image processing circuit 156 read out necessary illumination light control information and/or image processing information from the memory 137 based on the information on the observation mode transmitted from the input device 160, and operates based on necessary illumination light control information and/or image processing information.

The characteristic substance is, for example, a substance derived from the observation object contained in the observation object. The substance derived from the observation object may be, but not limited to, for example, hemoglobin.

The characteristic substance may also be, for example, an externally derived substance that is sprayed, administered, or applied to the observation object. The externally derived substance may be, for example, a dye used for living body observation. The dye may be, but not limited to, for example, Indigo Carmine, Crystal Violet, or Lugol's solution. Such dye is sprayed toward the observation object through a tube provided inside the endoscope apparatus. The spraying location and the concentration of dye, etc. are set based on the dye to be used, etc.

The externally derived substance may be a drug. The drug may be, but not limited to, a drug that accumulates in a tumor, etc., for example, a fluorescent marker, etc. By administering a fluorescent marker and observing with the illumination light having the wavelength emitted by the fluorescent marker, a lesion such as a tumor can be highlighted. Currently, various drugs are being developed. Administration is carried out by injection, drip infusion, and oral administration, etc.

In the case of an industrial endoscope apparatus, etc., it is also possible to apply and emphasize a medicine capable of emphasizing cracks and rusting.

The wavelength and light quantity ratio of the laser light emitted in each observation mode, the processing of the image processing circuit 156, etc., are programmed in advance, and are stored in the memory 137 provided in the main body 110. Instead of being provided in the main body 110, the memory 137 may be provided in the input device 160.

Laser light or narrow band light to be radiated to the observation object in order to observe the characteristic substance with good contrast is selected based on the absorption spectrum of the characteristic substance. That is, in order to observe hemoglobin with good contrast, laser light or narrow band light in a wavelength range where absorption by hemoglobin is comparatively high is radiated. Furthermore, in order to observe indigo carmine with good contrast, laser light or narrow band light in a wavelength range where absorption by indigo carmine is comparatively high is radiated.

Hereinafter, the five observation modes of the first embodiment will be described in order.

(1) White Observation Mode

The white observation mode is close to the so-called normal light observation mode, which is commonly used in the conventional endoscope observation. In this white observation mode, the illumination controller 136 turns on all of the laser light sources LD1 to LD4. The spectrum of the illumination light is a discrete spectrum peculiar to the laser as shown in FIG. 2, but has a color component in each of the RGB color ranges.

That is, as described above, the image sensor included in the imaging unit 152 used in the present embodiment is a CMOS image sensor having a Bayer array RGB color filter. Each of the RGB color ranges, in other words, the wavelength range of the R image, which is the R range; the wavelength range of the G image, which is the G range; and the wavelength range of the B image, which is the B range, are determined by a wavelength sensitivity range of the color filter mounted on the image sensor. In the present embodiment, the B range is a range having a wavelength from 400 to 480 nm, the G range is a range having a wavelength from 480 to 580 nm, and the R range is a range having a wavelength from 580 to 700 nm.

In the present embodiment, the R range contains red laser light having a wavelength of 635 nm emitted from the laser light source LD4, the Grange contains green laser light having a wavelength of 525 nm emitted from the laser light source LD3, and the B range contains blue-violet laser light having a wavelength of 405 nm emitted from the laser light source LD1 and blue laser light having a wavelength of 445 nm emitted from the laser light source LD2. As a result, the illumination light as a whole is white light.

The light quantity ratio of the laser light sources LD1 to LD4 can be appropriately adjusted depending on the observation object 190 and the spectral sensitivity characteristics of the imaging unit 152 mounted on the scope 120, in addition to the operator's preference, etc. For example, by setting the ratio of the light quantity Q1 of the laser light source LD1 (405 nm), the light quantity Q2 of the laser light source LD2 (445 nm), the light quantity Q3 of the laser light source LD3 (525 nm), and the light quantity Q4 of the laser light source LD4 (635 nm) to Q1:Q2:Q3:Q4=1:2:2:2, etc., the illumination light of generally white can be produced. Furthermore, it is also possible to set the light quantity ratio that is to be white by a general white balance method.

In the present observation mode, these rays of laser light are simultaneously emitted and radiated from the illuminating unit 146 toward the observation object 190. At this time, in order to simplify the control of the illumination light, light emission may be continuously performed, or, in consideration of power saving and image unevenness, etc., light may be turned off during a reading period of the image sensor.

The image information of the observation object 190 when the observation object 190 is irradiated with such substantially white illumination light is as follows. The illumination light of the laser light source LD1 (405 nm) and the laser light source LD2 (445 nm) is reflected and scattered by the observation object 190, enters the image sensor, and is detected to generate the B image. Similarly, the laser light source LD3 (525 nm) generates the G image, and the laser light source LD4 (635 nm) generates the R image. These RGB images are subjected to preset image processing by the image processing circuit 156. The display 170 displays the image information processed by the image processing circuit 156 as a color image of the observation object 190. As described above, the white observation mode is a mode in which all the laser light sources LD1 to LD4 emit light so that a general white image is acquired and observed.

Here, since all the light included in the white illumination light according to the present embodiment are laser light, their spectral line widths are extremely thin, even as thin as approximately 1 nm. This not only excels in monochromaticity, but also has a characteristic in that, in the case where it matches with the absorption characteristic of the characteristic substance contained in the observation object 190, as compared with an observation image of white illumination having a broad spectrum such as a widely used xenon lamp, the white observation mode can display the characteristic substance with good contrast.

The four characteristic substance observation modes will be described in order.

(2) One-Substance Observation Mode (Hemoglobin Emphasis Mode)

The present observation mode is an observation mode using illumination light having a wavelength matching the absorption characteristic of hemoglobin in order to observe with good contrast a region in which hemoglobin is abundant, in other words, a blood vessel.

Figure 3:
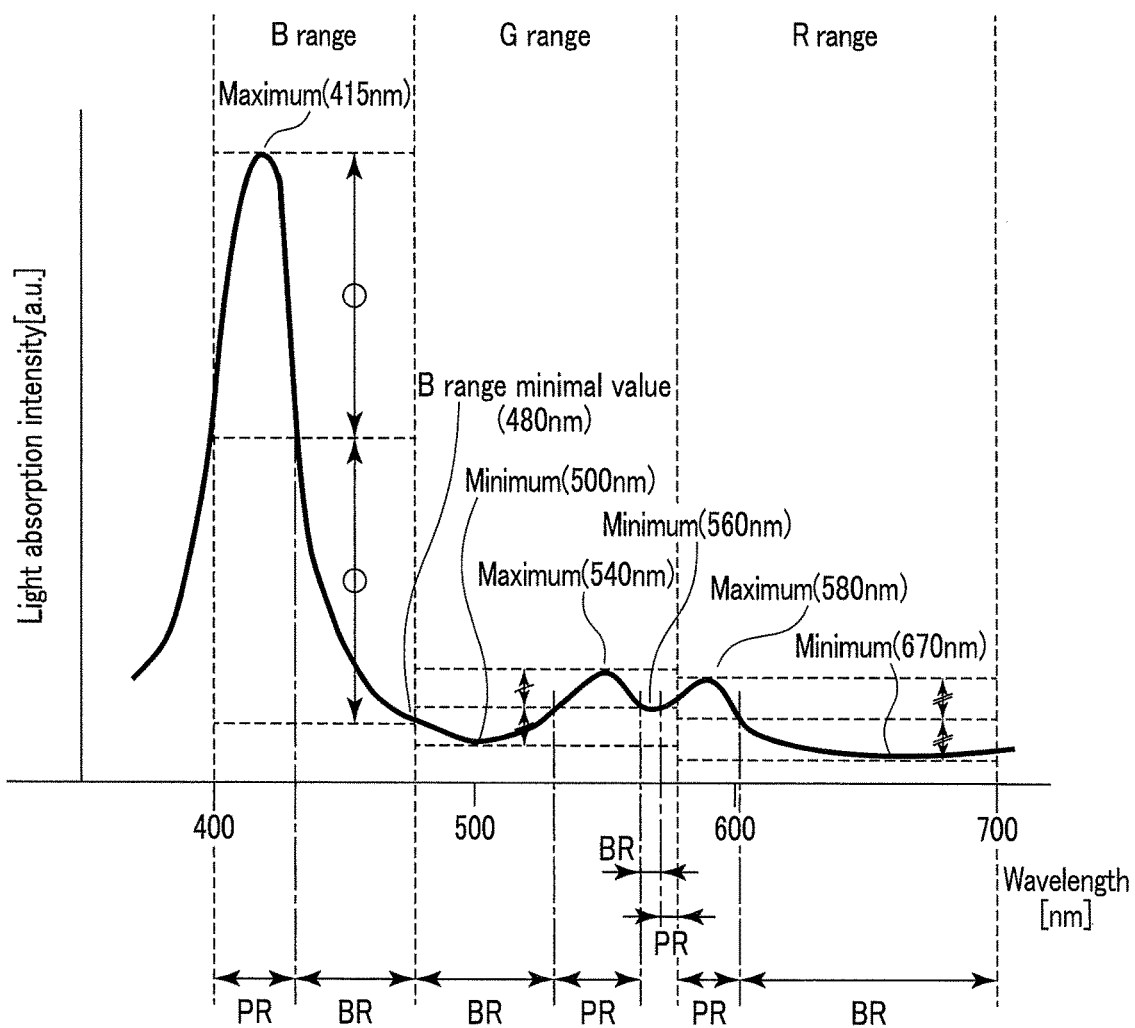
FIG. 3 shows an absorption spectrum of hemoglobin.

The absorption spectrum of hemoglobin has light absorption characteristics as shown in FIG. 3. That is, the absorption spectrum has a maximum value at wavelengths of 415 nm, 540 nm, and 580 nm, and has a minimum value at wavelengths of 500 nm, 560 nm, and 670 nm.

With respect to such absorption spectrum, ranges having high absorption, that is, absorption peak ranges PR, and absorption bottom ranges BR are defined by wavelength.

As described above, each of the RGB wavelength ranges in the present embodiment is such that, B range is a wavelength range from 400 to 480 nm, G range is a wavelength range from 480 to 580 nm, and R range is a wavelength range from 580 to 700 nm.

Based on the above, regarding each of the RGB wavelength ranges, when an intermediate value between the maximal value and the minimal value in the wavelength range is defined as a threshold value, as the light absorption intensity of hemoglobin, a range in which the light absorption intensity is higher than the threshold value is defined as an absorption peak range PR, and a range in which the light absorption intensity is lower than the threshold value is defined as an absorption bottom range BR. In other words, in each of the RGB color ranges, the wavelength range in which absorption of hemoglobin, which is a characteristic substance, is high or not is divided into the absorption peak range PR or the absorption bottom range BR depending on whether the light absorption intensity of hemoglobin is higher or lower than the intermediate value of each color range. Since the absorption peak range PR is a wavelength range in which absorption of hemoglobin is comparatively high in the color range, by using light in this wavelength range, a blood vessel containing a large quantity of hemoglobin absorbs more of this light, which enables acquiring a high-contrast image with respect to surrounding tissues as compared with light in the absorption bottom range BR. On the other hand, since the absorption bottom range BR is a wavelength range in which absorption of hemoglobin is comparatively low in the color range, by using light in this wavelength range, an image with a low contrast of blood vessels containing a large quantity of hemoglobin can be acquired.

In the present embodiment, as shown in FIG. 3, the absorption peak range PR is 400 to 440 nm in the B range, 520 to 555 nm and 570 to 580 nm in the G range, and 580 to 605 nm in the R range. In addition, the absorption bottom range BR is 440 to 480 nm in the B range, 480 to 520 nm and 555 to 570 nm in the G range, and from 605 to 700 nm in the R range.

In the present embodiment, as described above, emission wavelengths $\lambda 1$, $\lambda 2$, $\lambda 3$, and $\lambda 4$ of the laser light sources LD1, LD2, LD3, and LD4 are $\lambda 1=405$ nm, $\lambda 2=445$ nm, $\lambda 3=525$ nm, and $\lambda 4=635$ nm, respectively. Therefore, the emission wavelength $\lambda 1$ of the laser light source LD1 is included in the absorption peak range PR of the B range, and the emission wavelength $\lambda 3$ of the laser light source LD3 is included in the absorption peak range PR of the G range. Also, the emission wavelength $\lambda 2$ of the laser light source LD2 is included in the absorption bottom range BR of the B range, and the emission wavelength $\lambda 4$ of the laser light source LD4 is included in the absorption bottom range BR of the R range.

Of the one-substance observation modes, in the one-substance observation mode being a mode for highlighting hemoglobin (hemoglobin emphasis mode), the laser light source LD1 (405 nm) and the laser light source LD3 (525 nm) are turned on among the laser light sources LD1 to LD4. FIG. 4 shows the spectrum of illumination light in the one-substance observation mode (hemoglobin emphasis mode). By using such illumination light, it is possible to acquire an image with a high contrast of blood vessels that contain a large quantity of hemoglobin. Laser light having a wavelength of 405 nm and laser light having a wavelength of 525 nm are narrow band light selected based on the absorption spectrum of hemoglobin.

The light quantity ratio between the laser light sources LD1 and LD3 can be appropriately adjusted depending on the characteristics of the observation object 190, and the imaging unit 152 mounted on the scope 120, in addition to the operator's preference. For example, by setting the ratio of the light quantity Q1 of the laser light source LD1 (405 nm) and the light quantity Q3 of the laser light source LD3 (525 nm) to Q1:Q3=2:1 etc., capillary vessels in the surface layer can be observed with better contrast. This is due to the characteristic that light having a short wavelength is absorbed or scattered comparatively close to the surface of a living body, and light having a longer wavelength penetrates into a deeper layer and is absorbed or scattered. That is, as compared with the emission light (525 nm) from the laser light source LD3, since the emission light (405 nm) from the laser light source LD1 has many light components absorbed or scattered on the surface of the living body, it includes more image information of the capillary vessels in the surface layer of the living body. On the other hand, since the emission light (525 nm) from the laser light source LD3 travels from the middle layer to the deep layer of the living body and is absorbed or scattered, as compared with the emission light (405 nm) from the laser light source LD1, it includes information of fairly thick blood vessels from the middle layer to the deep layer.

Therefore, when it is desired to further improve the contrast of a blood vessel in a comparatively deep layer, for example, the ratio of the light quantity Q1 of the laser light source LD1 (405 nm) and the light quantity Q3 of the laser light source LD3 (525 nm) may be set to Q1:Q3=1:3, etc. When middle to deep layers are desired to be emphasized, it is easier to obtain the effect by emitting the light having a wavelength suitable for the layer to be emphasized more intensely than in the case where the surface layer is desired to be emphasized. In the present embodiment, the ratio of the light quantity Q1 of the laser light source LD1 (405 nm) to the light quantity Q3 of the laser light source LD3 (525 nm) is set as Q1:Q3=2:1 as the standard light quantity ratio on the basis of emphasizing the surface layer. It is also preferable to allow light quantity ratios to be selected, or to for allow the operator to arbitrarily set the light quantity ratio. Furthermore, it is also preferable to turn on only one of the laser light source LD1 or the laser light source LD3 and turn off the other, depending on the layer of the blood vessel desired to be observed.

In the present embodiment, in a similar manner as the white observation mode, these rays of laser light are emitted simultaneously, and are radiated toward the observation object 190 from the illuminating unit 146. In addition, whether to perform continuous light emission or to turn off the light during the readout period of the image sensor can be determined in the same manner as in the white observation mode. Whether or not to perform continuous light emission may be set the same as in the white observation mode, or may be set individually, such as performing continuous light emission for one of them, and turning off the other during the readout period.

In the one-substance observation mode (hemoglobin emphasis mode) in the present embodiment, only the laser light source LD1 and the laser light source LD3 are turned on, and the laser light source LD2 and the laser light source LD4 are turned off, but is not limited to this. For example, as a modification of the present embodiment, in addition to the laser light source LD1 and the laser light source LD3, the laser light source LD4 may also be turned on. This allows obtaining a natural color image including all RGB colors, in which the contrast of the surface layer and the middle to deep blood vessels is emphasized. Here, since it is comparatively difficult for the red light having the wavelength of 635 nm of the laser light source LD4 to be absorbed or scattered, the contrast of blood vessels containing hemoglobin is not impaired.

Furthermore, in addition to the laser light source LD1 and the laser light source LD3, the laser light source LD2 may also be turned on. This allows the color tone of the color image to be adjusted, the contrast of blood vessels in the surface layer to be suppressed, and the contrast of middle to deep blood vessels to be relatively improved. That is, when it is desired to improve the contrast of middle to deep blood vessels, assuming that the ratio of the light quantity Q1 of the laser light source LD1 to the light quantity Q3 of the laser light source LD3 is the light quantity ratio of Q1:Q3=1:3, in some cases, the image may be dark due to insufficient light quantity of the laser light source D1 on the surface layer. At this time, by adding the light of 445 nm of the laser light source LD2 and setting the ratio of the light quantities Q1, Q2, and Q3 of the laser light sources LD1, LD2, and LD3 to Q1:Q2:Q3=1:2:3, an image that is bright and has high contrast in the middle to the deep layer can be obtained. This is because, since the light of 445 nm of the laser light source LD2 is included in the absorption bottom range BR, it does not contribute to the contrast of the blood vessel, and allows the light quantity in the blue range to be improved.

Furthermore, all of the laser light sources LD1 to LD4 may be turned on. Here, in order to display with good contrast the blood vessels that contain large quantity of hemoglobin, it is preferable that the ratio of the light quantities Q1 to Q4 of the laser light sources LD1 to LD4 is adjusted to, for example, Q1:Q2:Q3:Q4=4:1:2:2. This allows both color tone and vascular visualization ability to be satisfied, and an image to be obtained that can observe the blood vessel with good contrast compared with the white observation mode.

Regarding such selection of the emission wavelength and the adjustment of the light quantity ratio, it is also preferable that such selection and adjustment can be performed by the operator himself/herself through the input device 160. It is also preferable that maintenance personnel can perform selection and adjustment using a hidden command, etc. Furthermore, it is also preferable that the selection and adjustment can be remotely performed by updating the firmware, etc.

Hemoglobin takes two states, that is, oxygenated hemoglobin bound to oxygen and reduced hemoglobin from which oxygen is desorbed. Although the absorption spectra of these two states are somewhat different, in consideration of the following points, in the present invention, the two states are considered as one characteristic substance.

- Both of hemoglobin in the two states are virtually present inside the blood vessel. That is, the region of presence is substantially equal, and only the presence ratio thereof is different.
- A region in which only one state is entirely present, and the other is not can hardly be seen inside the body.
- The state is reversibly changed from one to the other, and is not stabilized in either state.
- The peak wavelength and the bottom wavelength of the absorption spectrum are approximately equal.

As described above, substances whose absorption spectra are close to each other and existing locations that are substantially the same are regarded as one characteristic substance in the present invention.

(3) One-Substance Observation Mode (Indigo Carmine Emphasis Mode)

The present observation mode is an observation mode using illumination light having a wavelength matching the absorption characteristic of indigo carmine in order to observe with good contrast an area in which indigo carmine has accumulated, that is, a concave portion on the surface of the observation object 190, on the inner surface of the observation object 190.

Indigo carmine is a kind of dye solution that shows a dark blue color, and is used to emphasize irregularities on the surface of a living tissue using the accumulation thereof. That is, since indigo carmine accumulated in the concave portion shows the concave portion in dark blue, visibility of the concave portion is improved with respect to a convex portion and a flat portion showing a skin color to a red color. That is, this allows observation with good contrast. However, since the color of the living tissue is transparent through shallow concave portions, etc., sufficient contrast may not be obtained with ordinary white light in some cases. In such case, contrast can be improved by using the present observation mode as compared with the case of observation with ordinary white light.

The absorption spectrum of indigo carmine has light absorption characteristics as shown in FIG. 5. Similarly to hemoglobin, in the absorption spectrum of indigo carmine, an intermediate value between the maximal value and the minimal value of the light absorption intensity is set as a threshold value, and a wavelength range having a light absorption intensity higher than the threshold value is set as an absorption peak range PR, and a wavelength range having a light absorption intensity lower than the threshold value is set as an absorption bottom range BR.

However, as shown in FIG. 5, indigo carmine hardly absorbs light in the B range. That is, the difference between the maximal value and the minimal value of the light absorption intensity is smaller than those of the other two ranges. Also, no obvious peak (maximum) or bottom (minimum) is found. Therefore, the entire B range is defined as the absorption bottom range BR. In the case where it is considered that the contrast of the acquired image would not largely change regardless of which light in the wavelength range is used, it is preferable to set the entire color range as the absorption bottom range BR or the absorption peak range PR. Such a definition is suitable in a case where, for example, the difference between the maximal value and the minimal value of the light absorption intensity of the color range is equal to or less than a fraction as compared with the difference between the maximal value and the minimal value of the light absorption intensity in the other color ranges, and the absorption spectrum is gradual without an obvious peak (maximum) or bottom (minimum). It is particularly preferable in the case where the difference between the maximal value and the minimal value of the light absorption intensity of the color range is $1/10$ or less as compared with the difference between the maximal value and the minimal value of the light absorption intensity in the other color ranges.

On the other hand, as in the hemoglobin shown in FIG. 3, although the difference between the maximal value and the minimal value of the light absorption intensities in the G and R color ranges is equal to or less than a fraction as compared with the difference between the maximal value and the minimal value of the light absorption intensity in the B color range, in the case where clear peak wavelengths (540 nm, 580 nm) can be seen both in the G range and the R range, it is not preferable to define the entire range as the absorption bottom range BR. This is because, in the case where peaks (maximum) and bottoms (minimum) exist, images with significantly higher or lower contrast can be obtained in peaks and bottoms than light in the surrounding wavelengths.

As described above, indigo carmine emphasizes irregularities by accumulating in the concave portion. When the light in the wavelength range of the absorption peak range PR is used, since the light is absorbed in the concave portion where indigo carmine is accumulated, but is not absorbed at portions other than the concave portion, the contrast between the concave portion and the other portions can be improved than in the case of the white observation mode. On the other hand, when the light in the wavelength range of the absorption bottom range BR is used, since the light is hardly absorbed even in the concave portion where indigo carmine is accumulated, the contrast with a range other than the concave portion can be made lower than in the case of the white observation mode. That is, even after applying indigo carmine, an image with a contrast close to that of before the application of indigo carmine can be obtained.

The absorption peak range PR of indigo carmine according to the present embodiment does not exist in the B range, and is 550 to 580 nm in the G range, and 580 to 665 nm in the R range. Furthermore, the absorption bottom range BR is 400 to 480 nm, which is the entire range in the B range, 480 to 550 nm in the G range, and 665 to 700 nm in the R range.

In the present embodiment, as described above, the emission wavelengths $\lambda 1$ to $\lambda 4$ of the laser light sources LD1 to LD4 can irradiate laser light of $\lambda 1=405$ nm, $\lambda 2=445$ nm, $\lambda 3=525$ nm, and $\lambda 4=635$ nm, respectively. The emission wavelength $\lambda 1$ of the laser light source LD1 and the emission wavelength $\lambda 2$ of the laser light source LD2 are included in the absorption bottom range BR of the B range, and the emission wavelength $\lambda 3$ of the laser light source LD3 is included in the absorption bottom range BR of the G range. The emission wavelength $\lambda 4$ of the laser light source LD4 is included in the absorption peak range PR of the R range.

Figure 6:
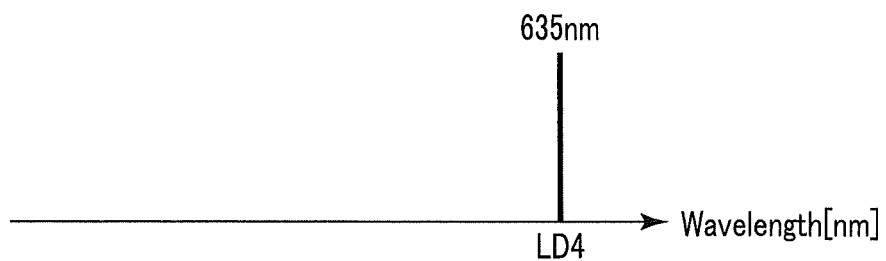
FIG. 6 shows a spectrum of illumination light in the one-substance observation mode (indigo carmine emphasis mode).

Of the one-substance observation modes, in the one-substance observation mode (indigo carmine emphasis mode) that highlights indigo carmine, only the laser light source LD4 (635 nm) is turned on among the laser light sources LD1 to LD4. FIG. 6 shows a spectrum of the illumination light in the one-substance observation mode (indigo carmine emphasis mode). This allows obtaining an image with good contrast of the concave portion where indigo carmine is accumulated. The laser light having a wavelength of 635 nm is narrow band light selected based on the absorption spectrum of indigo carmine.

Also in the present observation mode, in the same manner as the white observation mode and the one-substance observation mode (hemoglobin emphasis mode), whether to perform continuous emission or to turn off the light during the readout period of the image sensor is appropriately selectable.

In the one-substance observation mode (indigo carmine emphasis mode) in the present embodiment, only the laser light source LD4 is turned on, and the other laser light sources LD1, LD2, LD3 are turned off, which is not limited thereto. For example, at least one of the laser light source LD1 and the laser light source LD2, and the laser light source LD3 may be turned on. This allows obtaining a natural color image including all RGB colors in which the contrast of indigo carmine accumulated in the concave portion is emphasized. Here, as the light quantity ratio of each wavelength that is capable of satisfying both the color tone and the concave portion emphasis, the ratio of the light quantity Q1 of the laser light source LD1 (405 nm), the light quantity Q2 of the laser light source LD2 (445 nm), the light quantity Q3 of the laser light source LD3 (525 nm), and the light quantity Q4 of the laser light source LD4 (635 nm) is set to, for example, Q1:Q2:Q3:Q4=1:2:2:4, in which the light quantity of the laser light source LD4 is increased, which is different from the light quantity ratio Q1:Q2:Q3:Q4=1:2:2:2 used in the white observation mode.

(4) Two-Substance Observation Mode (Hemoglobin-Indigo Carmine Emphasis Mode)

The present observation mode is an observation mode suitable for observing the two characteristic substances of the observation object 190 at the same time with high contrast. In the present embodiment, in order to simultaneously observe blood vessels with large quantity of hemoglobin and a concave portion in which indigo carmine being a dye solution is accumulated, with a good contrast, an observation mode using illumination light having a wavelength matching the absorption characteristics of both hemoglobin and indigo carmine is provided.

In the present embodiment, as described above, emission wavelengths $\lambda 1$, $\lambda 2$, $\lambda 3$, and $\lambda 4$ of the laser light sources LD1, LD2, LD3, and LD4 are $\lambda 1=405$ nm, $\lambda 2=445$ nm, $\lambda 3=525$ nm, and $\lambda 4=635$ nm, respectively. The emission wavelength $\lambda 1$ (405 nm) of the laser light source LD1 and the emission wavelength $\lambda 3$ (525 nm) of the laser light source LD3 are included in the absorption peak range PR of hemoglobin. The emission wavelength $\lambda 4$ (635 nm) of the laser light source LD4 is included in the absorption peak range PR of indigo carmine. Therefore, as described above, the light emitted from the laser light source LD1 and the light emitted from the laser light source LD3 can express the hemoglobin with a good contrast, and the light emitted from the laser light source LD4 can express indigo carmine with a good contrast.

Figure 7:
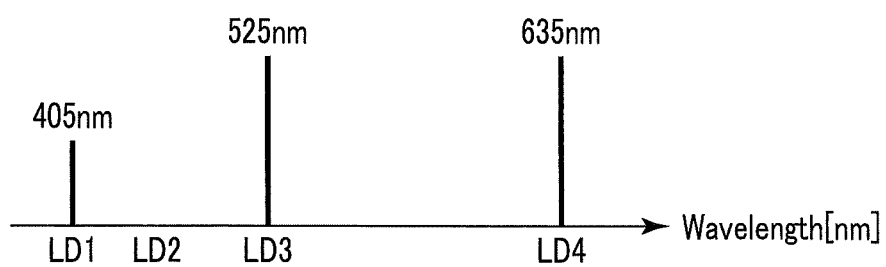
FIG. 7 shows a spectrum of illumination light in a two-substance observation mode (hemoglobin-indigo carmine emphasis mode).

In the present observation mode, the illumination controller 136 simultaneously turns on the laser light source LD1 (405 nm), the laser light source LD3 (525 nm), and the laser light source LD4 (635 nm). FIG. 7 shows the spectrum of the illumination light in the two-substance observation mode (hemoglobin-indigo carmine emphasis mode). The light quantity ratio is, for example, 2:1:2. This is because the light quantity ratio of the light emitted from the laser light source LD1 and the light emitted from the laser light source LD3 having a high absorption intensity of hemoglobin is set to 2:1, which is the ratio of emphasis on the superficial blood vessels, and the light quantity ratio of the light emitted from the laser light source LD1 and the light emitted from the laser light source LD4 is set to 1:1 (=2:2) so that the illumination light quantity of the B pixel range and the illumination light quantity of the R pixel range of the image sensor are substantially equal.

Here, in the case where the contrast of the two characteristic substances is desired to be equal to each other, the light quantity ratio described above is preferable. However, in the case where the contrast of either one of the characteristic substances is desired to be further improved, it is preferable to relatively increase the quantity of the narrow band light selected based on the absorption spectrum of the characteristic substance as compared with the narrow band light selected based on the absorption spectrum of the other characteristic substance. That is, when a characteristic substance whose contrast is desired to be improved is called a target characteristic substance, it is preferable to control the light source unit 132 so as to increase the quantity of the narrow band light selected based on the target characteristic substance as compared with the quantity of the narrow band light selected based on the other characteristic substance. In the present embodiment, for example, when hemoglobin is regarded as the target characteristic substance, by setting the ratio of the light quantities Q1, Q3, and Q4 of the laser light sources LD1, LD3, and LD4 to Q1:Q3:Q4=2:1:1, as compared with indigo carmine, hemoglobin can be observed with better contrast.

Here, it is preferable that the light quantity ratio can be continuously adjusted. Adjustment of the light quantity ratio can be performed, for example, by an operator inputting information through the input device 160.

In the case where the light receiving sensitivity of the image sensor in each RGB color range is different, it is also preferable to adjust the light quantity ratio in consideration thereof. Furthermore, in order to alleviate a sense of discomfort for an operator, it is also preferable to adjust the light quantity ratio so that the illumination light becomes close to white light.

When the laser light sources LD1, LD3, and LD4 are turned on simultaneously, each ray of laser light is radiated on the surface of the observation object 190 following the light guide path as described above. Furthermore, apart of the light reflected or scattered by the surface, etc., of the observation object 190 is detected by the imaging unit 152 and converted into an image signal. The image signal is transmitted to the image processing circuit 156 in the main body 110 through the image signal line 154. The image processing circuit 156 constructs image information of the observation object 190 based on each of these RGB image signals.

At this time, regarding the B image and the G image, it is possible to obtain image information equivalent to the B image and the G image in the aforementioned one-substance observation mode (hemoglobin emphasis mode). Regarding the R image, it is possible to obtain image information equivalent to the image of the one-substance observation mode (indigo carmine emphasis mode). That is, in the present observation mode, since each wavelength of the laser light is allocated to each RGB color range of the color filter of the image sensor, each of the B image and the G image with enhanced hemoglobin contrast and the indigo carmine-emphasized R image can be acquired independently and simultaneously.

Specifically, in each RGB image acquired in the present observation mode, the B image is an image in which the superficial blood vessels are emphasized by the laser light having a wavelength of 405 nm, and indigo carmine is not emphasized. The G image is an image in which middle to deep blood vessels are emphasized by the laser light having a wavelength of 525 nm, and indigo carmine is not emphasized. The R image is an image in which hemoglobin (blood vessel) is not emphasized by the laser light having a wavelength of 635 nm, but indigo carmine is emphasized.

In the present observation mode, by simultaneously turning on the laser light sources LD1, LD3, and LD4, both the hemoglobin-emphasized image and indigo carmine-emphasized image are acquired at the same time. Therefore, images with high contrast of two-characteristic substances can be acquired completely at the same time for the observation object 190 having motion and time variation, and the characteristic substance, etc. Therefore, occurrence of image blurring or color mis-registration is prevented, and even when displaying the images with high contrast of two characteristic substances in an overlapped manner or displaying them as color images, it provides no sense of discomfort.

The illumination light used in the present observation mode is similar to the illumination light used in the one-substance observation mode that considers color tones, such as a case in which red light having a wavelength of 635 nm is added to emit light in the one-substance observation mode (hemoglobin emphasis mode), or a case in which light having a wavelength of 405 nm and light having a wavelength of 525 nm are added to emit light in the one-substance observation mode (Indigo carmine emphasis mode). However, in this two-substance observation mode (hemoglobin-indigo carmine emphasis mode), the light quantity ratio is adjusted so that the main focus is placed on simultaneously observing both hemoglobin and indigo carmine at the same time with good contrast. In contrast, in the one-substance observation mode that considers the color tone, the light quantity ratio is adjusted so that the main focus is placed on adjusting the color tone. Both differ in this respect. However, as in the present embodiment, in the case where the contrast of the other party is not substantially affected, there may be cases in which the light quantity ratios are substantially equal between the two. In this case, only the image processing and the display mode to be described later on are different.

(5) Illumination Light Sequential Radiation Mode

The present observation mode is different from the above-described observation mode in which the observation purpose is clarified, and is a mode that acquires all of the images obtained by independently radiating all the laser light sources LD1 to LD4 of the light source unit 132 of the endoscope apparatus, and enables display of a desired image by image processing or a display mode, etc., described later on.

In the present embodiment, laser light having four wavelengths of the laser light sources LD1 to LD4 can be used. That is, laser light having a wavelength of 405 nm, laser light having a wavelength of 445 nm, laser light having a wavelength of 525 nm, and laser light having a wavelength of 635 nm can be used. The image sensor of the imaging unit 152 is a primary color imager of a RGB Bayer array, with the B range in a range having a wavelength from 400 to 480 nm, the G range in a range having a wavelength from 480 to 580 nm, and the R range in a range having a wavelength from 580 to 700 nm.

Figure 8:
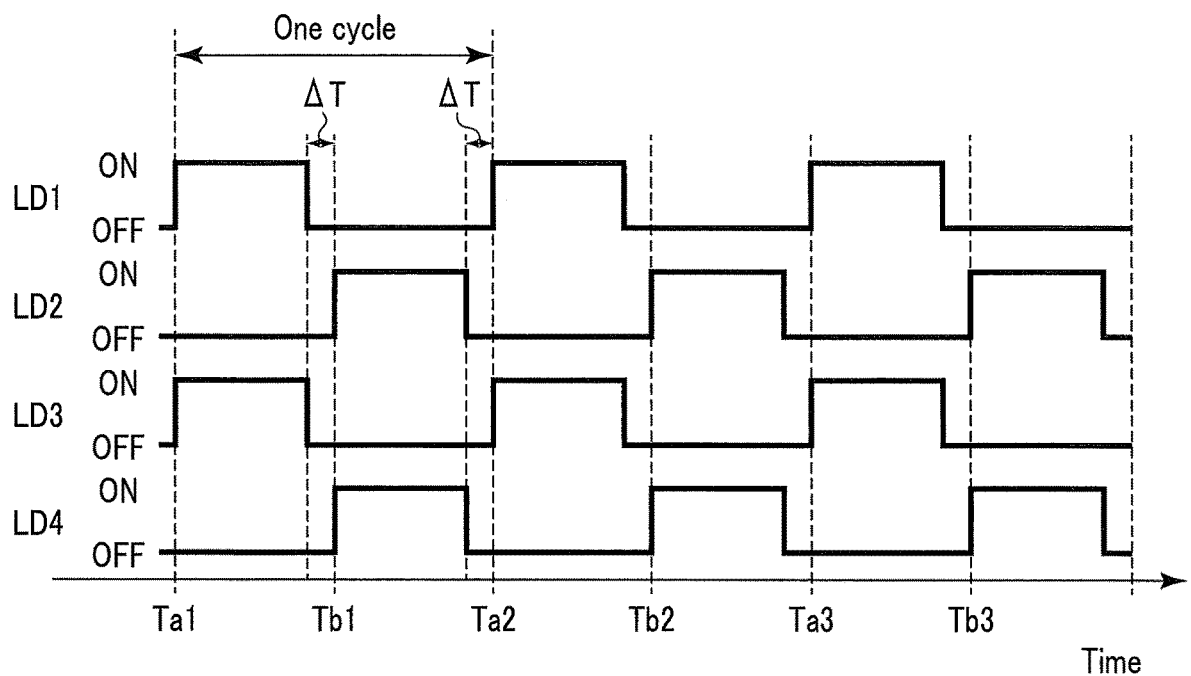
FIG. 8 is a timing chart of turning on and off laser light sources in an illumination light sequential radiation mode.

In the illumination light sequential radiation mode, the illumination controller 136 controls the laser light sources LD1 to LD4 to be turned on and off repeatedly at the timing shown in FIG. 8. The light emission timing of each of the laser light sources LD1 to LD4 is set based on the wavelength relationship of the laser light emitted from the laser light sources LD1 to LD4, and the spectral characteristics of the image sensor included in the imaging unit 152.

FIG. 8 is a timing chart that takes time on the horizontal axis, and shows the timings of turning on and turning off the laser light sources LD1 to LD4. In FIG. 8, when at the bottom of a rectangular wave-like chart, the light source is turned off, and when on the upper side, the light source is turned on. On the time axis, the timings at which any of the laser light sources LD1 to LD4 are turned on are indicated as Ta1, Tb1, Ta2, Tb2, Ta3, Tb3, . . . . Ta1, Tb1, Ta2, Tb2, Ta3, Tb3, . . . are periodic timings, in which the interval between Ta1 and Tb1, the interval between Tb1 and Ta2, . . . are equal to the frame rate of the image sensor. Also, at a timing corresponding to the readout time of the image sensor, all the laser light sources LD1 to LD4 are turned off.

In the present observation mode, the illumination controller 136 turns on the laser light source LD1 and the laser light source LD3 at a first timing Ta1, and turns on the laser light source LD2 and the laser light source LD4 at a second timing Tb1. One cycle is considered to be from the first timing Ta1 to the next first timing Ta2, in which each of the laser light sources LD1 to LD4 is repeatedly turned on and turned off.

Light having a wavelength of 405 nm emitted from the laser light source LD1 is included in the B range of the image sensor, and light having a wavelength of 525 nm emitted from the laser light source LD3 is included in the G range of the image sensor. Therefore, even if the laser light source LD1 and the laser light source LD3 are turned on simultaneously, they can be obtained as independent image information. Similarly, light having a wavelength of 445 nm emitted from the laser light source LD2 is included in the B range of the image sensor, and light having a wavelength of 635 nm emitted from the laser light source LD4 is included in the R range of the image sensor. Therefore, even if the laser light source LD2 and the laser light source LD4 are turned on simultaneously, they can be obtained as independent image information. As a result, by repeatedly turning on and turning off the laser light sources LD1 to LD4 at such timing, an image with a wavelength of 405 nm by the laser light source LD1, an image with a wavelength of 445 nm by the laser light source LD2, an image with a wavelength of 525 nm by the laser light source LD3, and the image with a wavelength of 635 nm by the laser light source LD4 can be independently acquired.

Actually, as long as the laser light source LD1 of 405 nm and the laser light source LD2 of 445 nm included in the same B range are turned on at different timings, the other laser light sources LD3 and LD4 may be turned on at any timing. In the present embodiment, in order to average the load of the image processing circuit 156, two laser light sources LD1 to LD4 are set to be turned on at respective timings.

Figure 9:
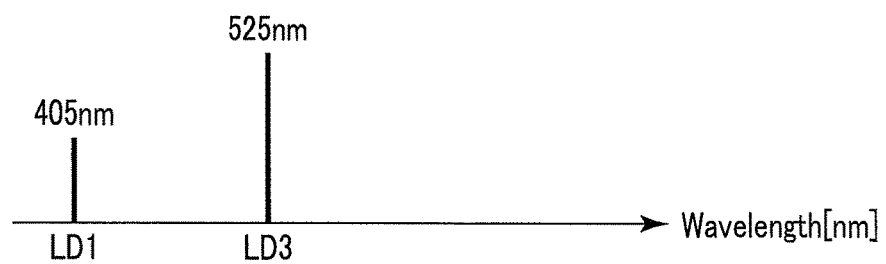
FIG. 9 shows an emission spectrum of a light source unit at a timing Ta1 shown in FIG. 8.

FIG. 9 shows the emission spectrum of the light source unit 132 at the timing Ta1, and FIG. 10 shows the emission spectrum of the light source unit 132 at the timing Tb1.

In this observation mode, since two images out of four images are imaged at different timings, for observation of the observation object 190 with fast movement and the observation object 190 with fast change, it is preferable that a high-speed imaging system is used and correction by image processing is applied.

With such a configuration, it is possible to construct images in all of the observation modes (1) to (4) described above by the image processing circuit 156 and display them on the display 170.

The above observation modes are examples, and can be applied in various manners, such as in a continuous image acquisition mode in which these observation modes are sequentially repeated, or in a light quantity ratio change image acquisition mode in which images of different light quantity ratios are sequentially repeatedly acquired in the same observation mode.

<Regarding Display Mode>

In the first embodiment of the present invention, display in various display modes is possible based on the observation mode described above.

The display mode is a mode for finally selecting an image the operator wishes to observe. The selected image is displayed on the display 170.

The display modes include an image number selection mode that selects how many observation images are to be displayed on the display 170 at the same time, and an image type selection mode that selects what kind of image is to be displayed. In other words, the display modes include an image number selection mode that selects the number of images to be simultaneously displayed on the display 170, and an image type selection mode that selects the type of image acquired in each observation mode to be displayed on the display 170. Both of these modes are selected by inputting information from the display mode selector 164. Information on the display mode input from the display mode selector 164 is transmitted to the image processing circuit 156.

Information on image types that can be displayed in each display mode is stored in advance in the memory 137. In each display mode, based on the information stored in advance in the memory 137, only the image types that can be displayed based on the selected observation mode are allowed to be selected.

The number of images can be freely selected except for limitations on monitor size, resolution, etc. For example, by increasing the number of the display 170, it is possible to simultaneously display the desired number of images. Basically, image types can be selected from the types of images that can be obtained by the endoscope apparatus. In addition, it is also possible to select the same image type that has a different time and observation place.

(A) Image Number Selection Mode

The image number selection mode in the present embodiment includes a single image display mode in which only one image is displayed, a two-image display mode in which two observation images are simultaneously displayed, and a multi-image display mode in which three or more images are simultaneously displayed. Furthermore, in the multi-image display mode, by inputting how many images to be displayed, the desired number of images can be input. Also, in the two-image display mode and the multi-image display mode, whether to display images in the same size, or to display one image or several images large, and the other images small, can be set in detail.

(B) Image Type Selection Mode

The image type selection mode in the present embodiment includes a direct display sub mode in which an image obtained in the above observation mode is directly displayed, and an image processing display sub mode in which predetermined image processing is performed based on image information obtained in the used observation mode.

In the direct display sub mode, of the observation modes described above, the images obtained in the four observation modes of (1) white observation mode, (2) one-substance observation mode (hemoglobin emphasis mode), (3) one-substance observation mode (indigo carmine emphasis mode), and (4) two-substance observation mode (hemoglobin indigo carmine emphasis mode), are directly displayed. In other words, an image to be displayed in the direct display sub mode is set depending on the type of the selected observation mode. In this mode, since the illumination light necessary for obtaining the image to be observed is radiated, and the image to which the necessary image processing is applied is directly displayed on the display 170, a desired image can be displayed efficiently without redundancy.

On the other hand, in the image processing display sub mode, a desired image can be obtained by applying appropriate image processing using the image information obtained in the selected observation mode. That is, the image in the selected observation mode can be displayed in the direct display sub mode; however, in the image processing display sub mode, the observation image other than in the selected observation mode can also be displayed. In addition, images that are not set in the observation mode can also be displayed.

For each observation mode, observation images that can be constructed and displayed in the image processing display sub mode are determined.

In (1) white observation mode, since an image is acquired by simultaneously emitting illumination light in which the ratio of the light quantities Q1, Q2, Q3, and Q4 of the laser light sources LD1 (405 nm), LD2 (445 nm), LD3 (525 nm), and LD4 (635 nm) is set to Q1:Q2:Q3:Q4=1:2:2:2, the B image is an image formed by the laser light source LD1 (405 nm) and the laser light source LD2 (445 nm), the G image is an image formed by the laser light source LD3 (525 nm), and the R image is an image formed by the laser light source LD4 (635 nm). Therefore, by using the R image out of the image information obtained in the white observation mode, an image of (3) one-substance observation mode (indigo carmine emphasis mode) can be displayed. In addition, for the purpose of improving the contrast of the middle to deep blood vessels and improving color tones and brightness as described in the one-substance observation mode, an image in the case of Q1:Q2:Q3=1:2:3 can be constructed and displayed. At this time, a desired image can be constructed and displayed by using the B image and the G image, and applying image processing to obtain an image in which the light quantity achieves an illumination in which the G image is 1.5 times brighter than the B image.

Furthermore, in the case of (2) one-substance observation mode (hemoglobin emphasis mode), that is, in the case where the emission spectrum is as shown in FIG. 4, the image processing display sub mode can display either one of an image in which only the superficial blood vessels are emphasized only by the B image (the image of only the laser light source LD1), or an image in which only the middle to deep blood vessels are emphasized only by the G image (the image of only the laser light source LD3). Furthermore, it also is possible to display an image in which the light quantity ratio differs from that of the direct display sub mode by use of the B image and the G image.

In the case of (3) one-substance observation mode (indigo carmine emphasis mode), since the emission spectrum is as shown in FIG. 6, the image is configured only by the R image by the laser light source LD4. Therefore, images other than those of the direct display sub mode cannot be obtained by the image processing display sub mode.

In the case of (4) the two-substance observation mode (hemoglobin-indigo carmine emphasis mode), as shown in FIG. 7, the B image is an image with a high contrast of the superficial blood vessel by laser light having a wavelength of 405 nm, the G image is an image with a high contrast of the middle to deep blood vessels by laser light having a wavelength of 525 nm, and the R image is an image with a high contrast of indigo carmine by laser light having a wavelength of 635 nm. Therefore, by the image processing display sub mode, an image of the one-substance observation mode (hemoglobin emphasis mode) can be obtained by using the B image and the G image, and an image of the one-substance observation mode (indigo carmine emphasis mode) can be obtained by using the R image. Furthermore, by performing image processing, an image in the case where the light quantity ratio of each laser light is different can be constructed. For example, by performing image processing to increase the light quantity of the G image, an image of the two-substance observation mode (hemoglobin-indigo carmine emphasis mode) in which the middle to deep hemoglobin is particularly emphasized can be obtained. Furthermore, by performing image processing to increase the light quantity of the R image, an image of a two-substance observation mode (hemoglobin-indigo carmine emphasis mode), in which the contrast of indigo carmine is particularly emphasized as compared with hemoglobin, can be obtained.

In (5) illumination light sequential radiation mode, images formed by the laser light sources LD1 to LD4 are acquired independently. Therefore, by selecting an appropriate image and performing image processing in which the light quantity ratio is changed in a pseudo manner so that an image having an appropriate light quantity ratio is obtained, all images that can be set in the observation mode can be realized.

In the image processing display sub mode as described above, information on which image can be constructed from which observation mode, what type of image processing can be used to construct the image, etc., and specific image processing processes and parameters are programmed in advance and stored, for example, in the memory 137 provided in the main body 110. Instead of being provided in the main body 110, the memory 137 may be provided in the input device 160. Alternatively, the function of the memory 137 may be distributed to two memories, and these two memories may be provided in the main body 110 and the input device 160, respectively.

After briefly explaining general blood vessel emphasis observation and indigo carmine dyeing observation, a specific display mode will be described.

First, the blood vessel emphasis observation will be described.

A technology that allows an operator to easily find a lesion by displaying a blood vessel emphasized image with illumination light in a wavelength easily absorbed by hemoglobin that is heavily present in the blood, which is so-called narrow band light, is used in various endoscopic apparatuses as NBI (Narrow Band Imaging). It is generally known that cancers differ from a group of capillary vessels in the surface layer or parts where the pattern thereof is normal. Therefore, by displaying with good contrast an observation object part of a patient or a subject, such as blood vessels of a stomach, esophagus, and large intestine, etc., or, particularly capillary vessels in the surface layer, an image that is easy to diagnose whether or not it is a cancer can be provided. The one-substance observation mode (hemoglobin emphasis mode) according to the present invention is an observation mode in which images are acquired by laser light of two wavelengths as an application of this NBI technology. By displaying the blood vessels, especially the capillary vessels of the surface layer with good contrast, an image that allows an operator to easily find cancer or distinguish normal tissue can be displayed.

The indigo carmine dyeing observation will be described.

On the mucosal surface of the stomach, esophagus, and large intestine, there are minute irregular patterns, which are called pit patterns. A method of determining the normal tissue and cancer, and, further, the degree of progress of cancer by the shape, etc., of the pit pattern is known as a pit pattern classification. The figure of the pit pattern classification is shown in FIG. 11 as a reference.

Indigo carmine is a representative dye agent most frequently used in recent years, which is sprayed during endoscopic examination and used to observe the pit pattern with good contrast. When diluted indigo carmine is applied to a lesion of the stomach, esophagus, or large intestine, irregularities of the surface of the observation object can be observed with good contrast.

Based on the above, a specific example of the display mode of the present embodiment will be described.

A case in which (4) the 2-substance observation mode (hemoglobin-indigo carmine emphasis mode) is selected as the observation mode, an image processing display sub mode is selected in the image type selection mode of the display mode, and an image in which the B image and the G image are configured with a light quantity ratio of 2:1 is displayed by the image processing, will be considered.

The image obtained at this time is basically the same image as the image in the case where (2) the one-substance observation mode (hemoglobin emphasis mode) is selected as the observation mode, and the direct display sub mode of the image type selection mode of the display mode is selected, which is in a mode that can display blood vessels containing hemoglobin with good contrast. Since the two-substance observation mode (hemoglobin-indigo carmine emphasis mode) is selected, indigo carmine is applied to the observation object 190. However, since both the wavelength of 405 nm and the wavelength of 525 nm are included in the absorption bottom range BR, the influence by indigo carmine is small, and an image in which the blood vessels can be observed with good contrast is displayed. An image of this image is shown in FIG. 12A.

Figure 12A:
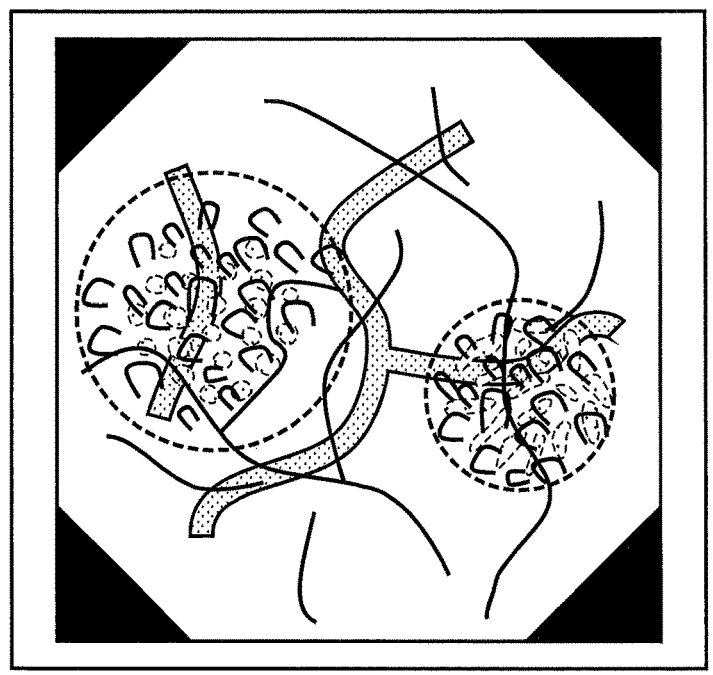
FIG. 12A shows an image configured by a B image and a G image in the two-substance observation mode (hemoglobin-indigo carmine emphasis mode).

FIG. 12A merely shows an image for explaining the function of the present embodiment, does not take medical precision into consideration, and does not indicate a medical function or diagnostic criteria. The same applies to the similar drawings mentioned below.

Similarly, a case of an image in which (4) the two-substance observation mode (hemoglobin-indigo carmine emphasis mode) is selected as the observation mode, an image processing display sub mode in the image type selection mode in the display mode is selected, and the R image is selected, will be considered. These modes obtain basically the same images as an image obtained with (3) the one-substance observation mode (Indigo Carmine emphasis mode), and are modes that can display the concave portion in which indigo carmine accumulates with good contrast. Also in this case, since the wavelength of 635 nm belongs to the absorption bottom range BR of hemoglobin, the contrast of the blood vessel is low, and the concave portion by indigo carmine can be displayed with high contrast, and observed. An image of this image is shown in FIG. 12B.

Furthermore, in the same observation mode, an example in which the image type selection mode of the display mode is the direct display sub mode is shown. In the case where the two-substance observation mode (hemoglobin-indigo carmine emphasis mode) is selected, as each piece of color information, three pieces of image information, such as the B image information by the laser light source LD1 (405 nm), the G image information by the laser light source LD3 (525 nm), and the R image information by the laser light source LD4 (635 nm), are obtained. An image configured by these RGB images is shown in FIG. 12C.

Figure 12B:
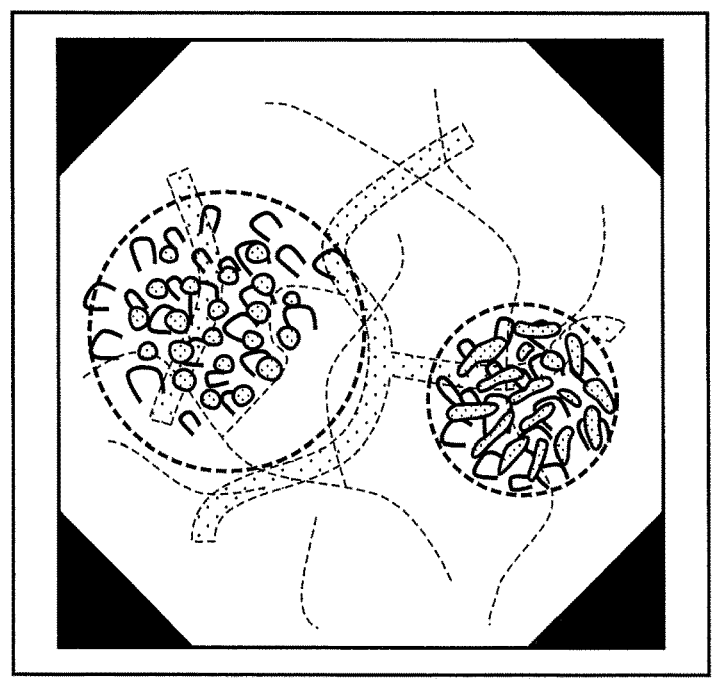
FIG. 12B shows an image configured by an R image in the two-substance observation mode (hemoglobin-indigo carmine emphasis mode).
Figure 12C:
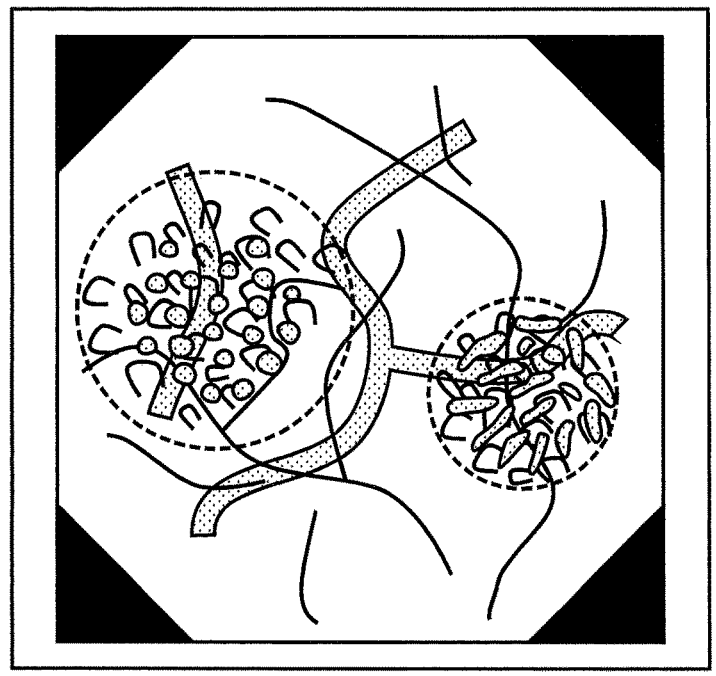
FIG. 12C shows an image configured by the R image, the G image, and the B image in the two-substance observation mode (hemoglobin-indigo carmine emphasis mode).

This image is an image obtained by overlapping FIG. 12A and FIG. 12B, in which both the blood vessel and indigo carmine are highlighted. At this time, the blood vessel is displayed as a red-colored image since it absorbs blue and green light. Indigo carmine is displayed as a blue-green colored image since it absorbs red light. Therefore, two characteristic substances are distinguished with good visibility and are observable.

In this display mode, since the lesion can be found by comparing both of the two characteristic substances on one screen, oversight is further reduced, which facilitates finding and diagnosing the lesion.

That is, in the image of FIG. 12A, in which the hemoglobin can be observed with good contrast, ranges in which an abnormal pattern of capillary vessels is suspected may be found in the two ranges surrounded by a dotted circle. Furthermore, in the image of FIG. 12B, in which indigo carmine can be observed with good contrast, since the pit pattern in the range surrounded by a dotted circle on the left can be determined as Type I shown in FIG. 11, this image can be determined as normal. On the other hand, the pit pattern in the range surrounded by a dotted circle on the right side is suspected to be type $III_L$ from FIG. 11, indicating a possibility of intra mucosal lesion (adenocarcinoma~M cancer). In this manner, it may be understood that by combining image modes in which two characteristic substances are displayed in good contrast with a region suspected of one lesion, it will be easier to find and diagnose the lesion.

In FIG. 12C, images in which the contrast of these two characteristic substances is emphasized can be displayed as one image. In FIG. 12C, first of all, when focusing on the capillary vessels, ranges that may possibly include two lesions are found. However, at the same time, when focusing on the pit pattern based on indigo carmine, it can be immediately determined that the range surrounded by the dotted circle on the left is normal. In this manner, in the observation mode that displays two characteristic substances at the same time, a time for comparing two images to determine whether or not they show the same place is unnecessary, which further expedites find and diagnosis.

On the other hand, in the observation modes of FIG. 12A and FIG. 12B, it is possible to find and diagnose the lesion by an image that emphasizes the contrast of one of the characteristic substances and is hardly influenced by the other characteristic substance. Therefore, each of the characteristic substances can be carefully and closely examined.

In the above manner, it is possible to carefully and closely examine each of the characteristic substances by switching and displaying images displaying only one characteristic substance. In addition, by overlapping and displaying two characteristic substances at the same time, it is possible to rapidly and easily find and diagnose lesions. Therefore, the display modes are switched in the above manner as appropriate based on various situations such as the condition of the lesions, the preference of the doctor, and the medical history of the patient, etc. In the present embodiment, the direct display mode is set as the default in the single display mode. However, the display mode and the display sub mode can be switched and selected easily by information input to the input device 160 by the operator.

[Characteristic Substance Region Extraction Function]

The endoscope apparatus according to the present embodiment has a function of automatically extracting a characteristic substance region based on the image information as shown in FIG. 12A to FIG. 12C. The term "characteristic substance region" refers to a region in which a characteristic substance exists and a region in which the group or pattern thereof is different from a normal part. The characteristic substance region is extracted by the image processing circuit 156 provided in the main body 110. That is, a characteristic substance region extractor is incorporated in the image processing circuit 156, which allows extracting an appropriate image from the image information transmitted from the imaging unit 152, and to extract the characteristic substance region by using generally-known pattern recognition or image analysis techniques. The characteristic substance region extractor is configured as, for example, the software recorded in the memory 137 provided in the main body 110, the electric circuit provided in the image processing circuit 156, and an external memory that is provided outside the main body 110 and is connected to the main body 110 through a signal line, etc. or as a complex thereof. The characteristic substance region extractor has an algorithm that extracts a characteristic substance region by comparing a specific portion of the image information of the observation object 190, that is, a region where the contrast of the characteristic substance is particularly high, or a group of high-contrast regions and their patterns, with that of a normal region, by conventional pattern recognition and image analysis technology, etc. The characteristic substance region extractor roughly extracts a region in which the contrast of the characteristic substance is particularly high, or an entire region in which a group of regions with high contrast or a pattern thereof is different from that in a normal region. Examples are shown in FIG. 13A, FIG. 13B, and FIG. 13C.

Figure 13A:
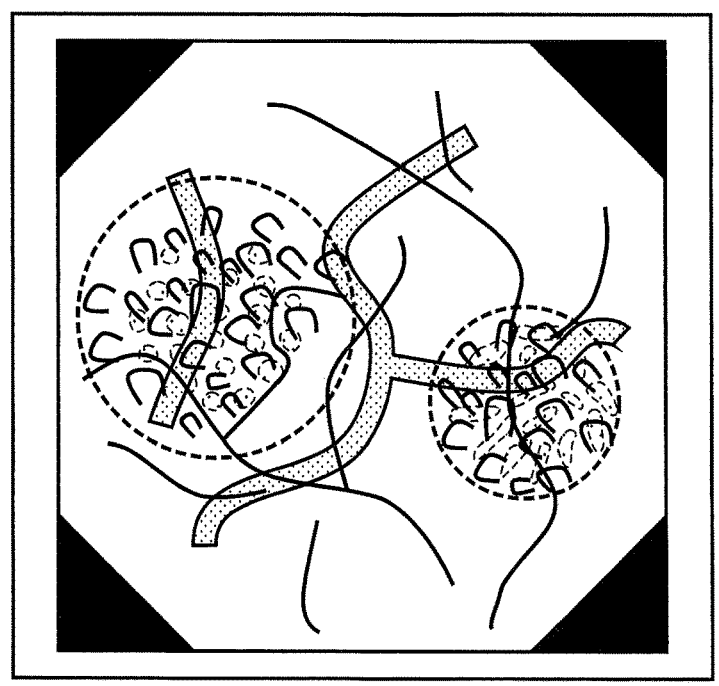
FIG. 13A shows an image in which blood vessels based on hemoglobin are emphasized, corresponding to FIG. 12A.

FIG. 13A to FIG. 13C show a case in which the same observation object 190 is observed in the same observation mode and display mode as that of the examples described with reference to FIG. 12A to FIG. 12C. That is, FIG. 13A shows an image corresponding to FIG. 12A, in which blood vessels based on hemoglobin are emphasized, FIG. 13B shows an image corresponding to FIG. 12B, in which indigo carmine is emphasized, and FIG. 13C shows an image corresponding to FIG. 12C, in which both a blood vessel and indigo carmine are emphasized.

In FIG. 13A, a region in which a group of superficial blood vessels or a pattern thereof is different from that of a normal region exists, and the characteristic substance region extractor extracts two regions that are surrounded by a dotted circle in FIG. 13A as characteristic substance regions. FIG. 13B shows an image in which the scattered indigo carmine is accumulated in the concave portion on the surface of the observation object 190, allowing the pit pattern to be observed with good contrast. Based on this image, the characteristic substance region extractor extracts a region of a pit pattern that is different from normal and is surrounded by a dotted circle shown on the right side of FIG. 13B as a characteristic substance region. On the other hand, for the region on the left side of FIG. 13B, which is determined as being different from normal in the superficial blood vessel image (FIG. 13A), since the pit pattern is normal, the characteristic substance extractor judges this to be normal and extracts only one region that is surrounded by a dotted circle shown on the right side as a characteristic substance region.

As described above, the characteristic substance region extractor displays the image of FIG. 13A obtained by extracting hemoglobin as a characteristic substance, and the image of FIG. 13B obtained by extracting indigo carmine as a characteristic substance as the characteristic substance region image. Here, the image is displayed so as to enhance visibility by surrounding the characteristic substance region with a dotted circle, by using an arrow in the manner shown in FIG. 13D, or by lowering the brightness of the peripheral region in the manner shown in FIG. 13E.

This characteristic substance region image may also be displayed using a monochrome image from which the extraction of the characteristic substance is originated, such as, in the case of hemoglobin, only the image obtained by laser light having a wavelength of 405 nm, and, in the case of indigo carmine, only the image obtained by laser light having a wavelength of 635 nm. Other images, such as an image formed by laser light having a wavelength of 445 nm and an image formed by laser light having a wavelength of 525 nm, may also be combined to be displayed as color images.

FIG. 13C is an image displaying overlapping regions of characteristic substance regions, that is, a characteristic substance overlapping region, extracted based on images of both hemoglobin and indigo carmine, that is, the image of FIG. 13A and the image of FIG. 13B.

In the example of the present embodiment, since the region on the right side of the characteristic substance region based on hemoglobin (FIG. 13A) and the characteristic substance overlapping range of indigo carmine (FIG. 13B) are substantially equal regions, the shape of the characteristic substance overlapping region is almost unchanged.

The characteristic substance extractor has a function of calculating and displaying the overlapping region of the characteristic substance region based on different characteristic substances by using a generally-known image processing technology, etc. In the case where the characteristic substance regions of two characteristic substances are different, the characteristic substance overlapping region is defined as a region where both characteristic substances are present. Therefore, in the case where no overlapping region exists, there may be a case in which no characteristic substance overlapping region exists even though characteristic substance regions for individual characteristic substances exist.

Figure 14A:
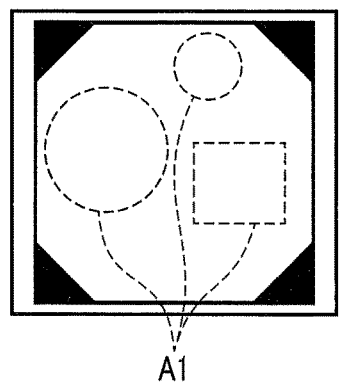
FIG. 14A is an image diagram of a characteristic substance region of a first characteristic substance.
Figure 14B:
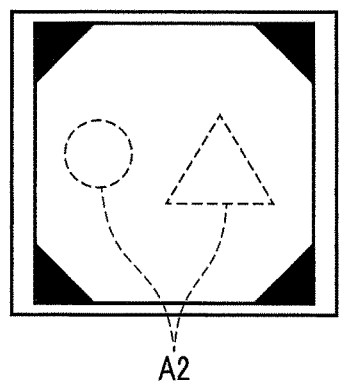
FIG. 14B is an image diagram of a characteristic substance region of a second characteristic substance.
Figure 14C:
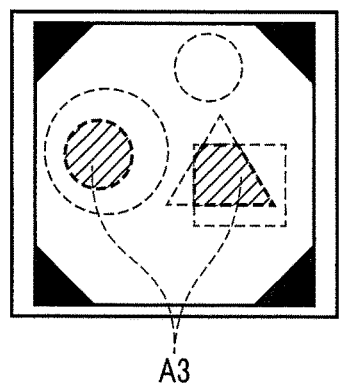
FIG. 14C shows a characteristic substance overlapping range of the first characteristic substance and the second characteristic substance.

FIG. 14A to FIG. 14C are image diagrams of the characteristic substance overlapping region. FIG. 14A is an image diagram of a characteristic substance region of a first characteristic substance. In this image diagram, three characteristic substance regions A1 of a first substance exist. Similarly, FIG. 14B is an image diagram of a characteristic substance region of a second characteristic substance. In this image diagram, two characteristic substances regions A2 of a second substance exist. FIG. 14C shows a characteristic substance overlapping region of the first characteristic substance and the second characteristic substance. A characteristic substance overlapping region A3 is an overlap of the characteristic substance regions A1 and A2 of both of the two characteristic substances.

[Operation, Effect]

The above configuration allows the characteristic substance included in the observation object 190 to be captured with good visibility. Particularly, since narrow band light (several nm or less in spectral line width) obtained by a semiconductor laser element selected based on the absorption peak range and bottom range of the characteristic substance is used, the characteristic substance can be displayed and observed with good contrast.

Furthermore, by using various observation modes, an operator can directly observe a desired image. In addition, an endoscope apparatus configured to easily acquire necessary images according to user preferences and circumstances, such as image construction by image processing after completion of observation, can be obtained. Particularly, after completion of observation, it is possible to display the characteristic substance of the suspected lesion portion with good contrast, or to observe the characteristic substance with good contrast retroactively to the previous examination in a scene such as follow-up observation.

Particularly, in the case where it is clear in advance that the characteristic substance to be observed or the observation mode is, such observation mode (the above observation modes (1) to (4)) may be used. In the case of wishing to evaluate various images after observation, by using the illumination light sequential evaluation mode, a desired image can be acquired even afterwards.

In addition, by using various display modes, the operator can compare and examine desired images with a desired comparison method. Since a switchable display and over-lapped display for two characteristic substances can be provided, it is possible to provide an environment where diagnosis and medical evaluation are easily performed. In addition, since the characteristic substance overlapping region can be automatically displayed, the examination time and the evaluation time of the image can be reduced.

As described above, according to the present embodiment, observation can be performed efficiently.

Modification of First Embodiment

In the first embodiment, when defining the absorption peak range and the absorption bottom range based on the absorption spectra of indigo carmine and hemoglobin, an intermediate value between the maximal intensity and the minimal intensity of each color range is defined as a threshold value, and a range beyond that is defined as an absorption peak range, and a range below that is defined as an absorption bottom range. However, the way of defining the absorption peak range and the absorption bottom range is not limited thereto.

In the present modification, when the absorption intensity of ⅓ and the absorption intensity of ⅔ of the difference between the maximal intensity and the minimal intensity of each color range are defined as "⅓ intensity reference" and "⅔ intensity reference", respectively, a wavelength range having an absorption intensity equal to or higher than the ⅔ intensity reference is defined as an absorption peak range PR, a range that is equal to or less than the ⅓ intensity reference is defined as an absorption bottom range BR, and a range therebetween is defined as an absorption middle range MR. This point is different from the first embodiment.

FIG. 15 shows the absorption peak range PR, the absorption bottom range BR, and the absorption middle range MR defined in accordance with this reference for the absorption spectrum of indigo carmine. As in the first embodiment, since the absorption intensity of the B range is significantly lower than that of the G range and the R range, the entire range is defined as the absorption bottom range BR. A range not included in either of the absorption peak range PR or the absorption bottom range BR is defined as an absorption middle range MR.

In the B range, the absorption bottom range BR is a wavelength range from 400 to 480 nm. This is the entire range of the B range.

In the G range, the absorption peak range PR is a wavelength range from 555 to 580 nm, the absorption bottom range BR is a wavelength range from 480 to 545 nm, and the absorption middle range MR is a wavelength range from 545 to 555 nm.

In the R range, the absorption peak range PR is a wavelength range from 590 to 650 nm, the absorption bottom range BR is a wavelength range from 675 to 700 nm, and the absorption middle range MR is a wavelength range from 580 to 590 nm and a wavelength range from 650 to 675 nm.

With such configuration, the absorption peak range PR is defined as a range having a higher absorption intensity, and the absorption bottom range BR is defined as a range having a lower absorption intensity. Therefore, by using narrow band light of wavelengths included in the absorption peak range PR and the absorption bottom range BR defined in the present modification, an image with higher contrast can be obtained than in the case of using narrow band light included in the absorption peak range in the definition of the first embodiment, but not included in the absorption peak range in the definition of the present modification. Similarly, for the absorption bottom range BR, it is also possible to obtain an image in which the contrast is suppressed to be lower.

In the present embodiment and its modification, an example in which an image sensor having an RGB Bayer array is used as the image sensor of the imaging unit 152 has been described; however, the present invention is not limited thereto. For example, for the image sensor of the imaging unit 152, it is possible to use an image sensor having a complementary color filter, which is generally used.

An example of a spectrum of light transmittance of a primary color filter is shown in FIG. 16. The primary color filter has three color filters of an R filter, a G filter, and a B filter. The R filter, the G filter, and the B filter have light transmission characteristics as shown in FIG. 16, respectively. That is, the R filter has a characteristic of transmitting light in the red range, but not light in the other color ranges; the G filter has a characteristic of transmitting light in the green range, but not light in the other color ranges; and the B filter has a characteristic of transmitting light in the blue range, but not light in the other color ranges. Thus, the illumination light reflected and scattered by the observation object 190 as in the above-described embodiment and its modification can be separately detected in the three color ranges of the R range, the G range, and the B range.

As shown in FIG. 16, the light transmittance of an actual primary color filter has overlaps in its boundary ranges. Light in this overlapping range is detected in both of two adjacent color ranges. For example, light having a wavelength of 500 nm is detected in both the blue range and the green range. In the case of narrow band light such as laser light, by utilizing this characteristic, it is possible to improve the brightness of the image. That is, since the light in the overlapping range of the filter, such as light having a wavelength of 500 nm, is detected in both of the two color ranges, such light allows the image to be brighter than the light detected only in one color range. This method is particularly effective in the white observation mode. On the other hand, in the case where emphasis of the characteristic substance of the observation object 190 is desired, the light detected in both of the two color ranges increases the emphasis level in both color ranges. For this reason, it is also effective in the case of improving the emphasis of characteristic substances. However, as described above, in the case where it is desired to emphasize only the surface layer and not the middle or lower layer, it is desirable to emphasize only the image of the blue range that easily absorbs the light of the surface layer, without emphasizing the image of the green range and the red range absorbed by the middle or lower layer. In such a case, it is preferable to use light on a wavelength side shorter than 480 nm that tends to be strongly absorbed in the blue range, rather than the light in the overlapping range.

An example of the light transmission spectrum of the complementary color filter is shown in FIG. 17. The complementary color filter includes a four color filter including: a three color filter that separately acquires the light of the three color ranges of an M (Magenta) range that transmits light in the blue range and the red range, but does not transmit light in the green range, a C (Cyan) range that transmits light in the blue range and the green range, but does not transmit light in the red range, and a Y (Yellow) range that transmits light in the green range and the red range, but does not transmit light in the blue range; and a G filter that transmits light in the green range, but does not transmit light in the blue range and the red range. Generally, a G filter having the same light transmission spectrum as the G filter of the primary color filter shown in FIG. 17 is used.

An image sensor having the complementary color filter uses such four color filters; however, by calculation, it is able to obtain image information of three colors of R image information, G image information, and B image information. Therefore, in the first embodiment and the modification of the present invention, even in the case of using an image sensor having a complementary color filter as the image sensor of the imaging unit 152, it can be accommodated without needing to change the emission spectrum, timing, etc., of the illumination light, by simply changing the processing function of the image processing circuit 156 of the main body 110 from the primary color filter to the complementary color filter. As for the calculation of the complementary color filter, a commonly used calculation can be used.

An image sensor having an MCY color filter is called as a complementary color filter type image sensor. The imaging unit 152 including the complementary color filter type image sensor configures an imaging system configured to separately acquire the R image, the G image, and the B image in cooperation with the image processing circuit 156. The complementary color filter type image sensor comprises M pixels that are color pixels configured to separately acquire light in the M range, C pixels that are color pixels configured to separately acquire light in the C range, and Y pixels that are color pixels configured to separately acquire light in the Y range. The image processing circuit 156 performs image processing that separately acquires the R image, the G image, and the B image based on the image information acquired by the M pixels, the C pixels, and the Y pixels.

It is also possible to use a monochrome type image sensor not having a color filter as the image sensor of the imaging unit 152. Although the monochrome type image sensor is equipped with an ultraviolet/infrared cutoff filter that removes infrared rays and ultraviolet rays as necessary, it receives light in the wavelength range from 400 nm to 700 nm, which is light in the visible range. For this reason, the light in the wavelength described as being separated and received by the filter of the image sensor in the above-described embodiment and modification needs to be emitted at different timings. In the case of using a monochrome type image sensor, in order to obtain a color image, it is necessary to at least emit the light of the red range, the green range, and the blue range at different timings, respectively. For example, in the case of using narrow band light of four colors having a wavelength of 405 nm, a wavelength of 445 nm, a wavelength of 525 nm, and a wavelength of 635 nm as in the first embodiment, even in the white observation mode, radiation is repeatedly performed in sequence at a first timing at which only light having two wavelengths of 405 nm and 445 nm, which is the light in the blue range, is radiated, a second timing at which only light having a wavelength of 525 nm, which is the light in the green range, is irradiated, and a third timing at which only light having a wavelength of 635 nm, which is the light in the red range, is irradiated. In this case, the imaging unit 152 cooperates with the light source unit 132, the driver 134, the illumination controller 136, and the image processing circuit 156 to configure an imaging system configured to separately acquire the R image, the G image, and the B image.

The monochrome type image sensor is preferably used in (5) sequential radiation mode. In the case of the monochrome type image sensor, since colors are switched by illumination light, an image in which colors are clearly separated, and not mixed, can be obtained. In the primary color and the complementary color filters, although there is some loss because the transmittance of light to be transmitted is not 100%, in the monochrome type, a higher transmittance can be secured in comparison thereto. Furthermore, since images are obtained one by one for each color and each wavelength in all the pixels of the image sensor, resolution can be improved. In a primary color Bayer, ¼ of all pixels are respectively assigned to R pixels and B pixels, and the remaining half of all pixels is assigned to G pixels. This also applies in the case of the complementary color filter.

Second Embodiment

A second embodiment of the present invention will be described with reference to the drawings. Explanations will be given for the portions different from the first embodiment, and will be omitted for the same portions.

In the present embodiment, the configuration of a light source unit 132 is different from that of the first embodiment; therefore, an illumination controller 136 and an image processing circuit 156, and information stored in a memory 137 are different from those in the first embodiment.

In the present embodiment, the light source unit 132 includes a laser light source LD5 in addition to the laser light sources LD1 to LD4 of the first embodiment. The characteristics of the laser light sources LD1 to LD5 are as follows.

The laser light source LD1 is configured to emit blue-violet laser light having a wavelength of 405 nm. The output is approximately 1.5 W.

The laser light source LD2 is configured to emit blue laser light having a wavelength of 445 nm. The output is approximately 3 W.

The laser light source LD3 is configured to emit green laser light having a wavelength of 525 nm. The output is approximately 3 W.

The laser light source LD4 is configured to emit red laser light having a wavelength of 635 nm. The output is approximately 3 W.

The laser light source LD5 is configured to emit orange laser light having a wavelength of 590 nm. The output is approximately 2 W.

The laser light sources LD1 to LD4 are direct-emission type semiconductor laser light sources LD1 to LD4 configured to directly emit light of a target wavelength. However, the laser light source LD5 is a semiconductor laser of a Secondary Harmonic Generation (SHG) type composed of an infrared semiconductor laser configured to emit infrared rays of 1180 nm, which are twice the wavelength, and a nonlinear optical crystal configured to halve the wavelength.

FIG. 18 shows a light spectrum that can be emitted by the light source unit 132 in the second embodiment. As shown in FIG. 18, in the present embodiment, two wavelengths (laser light source LD1 and laser light source LD2) are allocated to a blue range (400 to 480 nm), one wavelength (laser light source LD3) is allocated to a green range (480 to 580 nm), and two wavelengths (laser light source LD4 and laser light source LD5) are allocated to a red range (580 to 700 nm).

In the embodiment, in addition to hemoglobin and indigo carmine, crystal violet is assumed as a characteristic substance. Crystal violet is a drug that dyes the nucleus of a cell and is a dye used for observation by an enlarged endoscope apparatus. As the crystal violet is applied, a lesion discolors to blue, and a pattern on a surface also is raised. Therefore, by observing the pattern of this pattern with the enlarged endoscope apparatus, the nature (benign/malignant, etc.) of the lesion can be determined.

<Observation Mode>

An observation mode in the present embodiment is different from that in the first embodiment in that a one-substance observation mode (crystal violet emphasis mode) is further added to the observation modes described in the first embodiment. The one-substance observation mode (crystal violet emphasis mode) will be described.

(6) One-Substance Observation Mode (Crystal Violet Emphasis Mode)

The present observation mode is an observation mode using illumination light having a wavelength matching to the absorption characteristic of crystal violet in order to observe a region dyed with crystal violet, that is, a pattern is discolored in blue and emerges, on the inner surface of an observation object 190 with good contrast.

Crystal violet is a kind of dye solution and exhibits a bluish purple color, and is used for observing the pattern of the pattern dyed thereby on the inner surface of the observation object 190. That is, crystal violet selectively dyes the nucleus of a cell, and what is distributed appears to emerge as a pattern. Since the pattern of this pattern differs depending on the nature (benign/malignant etc.) of the lesion, it becomes possible to observe the markings of this pattern with the enlarged endoscope apparatus to determine the nature of the lesion.

The absorption spectrum of crystal violet has light absorption characteristics as shown in FIG. 19. In the same manner as in the first embodiment, in the absorption spectrum of crystal violet, an intermediate value between a maximal value and a minimal value of a light absorption intensity is set as a threshold value, and a wavelength range having a light absorption intensity higher than the threshold value is set as an absorption peak range PR, and a wavelength range having a light absorption intensity lower than the threshold value is set as an absorption bottom range BR. However, as can be seen from FIG. 19, crystal violet hardly absorbs light in the B range. That is, the difference between the maximal value and the minimal value of the light absorption intensity is smaller than those of the other two ranges. Also, no obvious peak (maximum) or bottom (minimum) is found. Therefore, the entire B range is defined as an absorption bottom range BR.

As mentioned earlier, the pattern emerges by dyeing the nucleus of a cell with crystal violet. Since the light in the wavelength range of the absorption peak range PR is absorbed in the range dyed with crystal violet, and is not absorbed in the region that is not dyed with crystal violet, the contrast between these two regions can be improved more than in the case of a white observation mode. On the other hand, since the light in the wavelength range of the absorption bottom range BR is hardly absorbed even in the region dyed with crystal violet, the contrast between the dyed region and the region not dyed can be made lower than in the case of the white observation mode. That is, even after applying the crystal violet, it is possible to obtain an image with a contrast close to that before applying the crystal violet.

According to FIG. 19, the absorption peak range PR and the absorption bottom range BR of the crystal violet are as follows.

In the B range, the absorption bottom range BR is a wavelength range from 400 to 480 nm. This is the entire range of the B range.

In the G range, the absorption peak range PR is a wavelength range from 535 to 580 nm, and the absorption bottom range BR is a wavelength range from 480 to 535 nm.

In the R range, the absorption peak range PR is a wavelength range from 580 to 610 nm, and the absorption bottom range BR is a wavelength range from 610 to 700 nm.

Therefore, in the present embodiment, an emission wavelength (405 nm) of the laser light source LD1, an emission wavelength (445 nm) of the laser light source LD2, an emission wavelength (525 nm) of the laser light source LD3, and an emission wavelength (635 nm) of the laser light source LD4 are included in the absorption bottom ranges BR, and an emission wavelength (590 nm) of the laser light source LD 5 is included in the absorption peak range PR.

The spectrum of the illumination light in the one-substance observation mode (crystal violet emphasis mode) is shown in FIG. 20. As shown in FIG. 20, in the one-substance observation mode (crystal violet emphasis mode), only the laser of the laser light source LD5 (590 nm) among the laser light sources LD1 to LD 5 is turned on. As a result, a pattern of the pattern dyed with crystal violet can be observed with good contrast. Laser light having a wavelength of 590 nm is narrow band light selected based on the absorption spectrum of crystal violet.

Also in the present observation mode, in the same manner as that described in the first embodiment, whether to perform continuous emission or to turn off the light during a readout period of an image sensor is a matter selectable as appropriate.

In the one-substance observation mode (crystal violet emphasis mode) in the present embodiment, although only the laser light source LD5 is turned on, and the other laser light sources LD1 to LD4 are turned off, the present invention is not limited thereto. For example, by turning on at least one of the laser light source LD1 and the laser light source LD2, and the laser light source LD3, it is possible to obtain a natural color image including all colors of RGB, in which the contrast of the range dyed with crystal violet is emphasized.

Furthermore, as compared with (1) white observation mode described in the first embodiment, in (1) white observation mode according to the present embodiment, since light having a wavelength of 590 nm that is an orange range is added, a white image with improved color reproducibility can be obtained. That is, although, in the first embodiment, the light in the range between green of 525 nm and red of 635 nm is missing, in the present embodiment, since the light of 590 nm is added, it is possible to improve the color reproducibility of the observation object 190 from yellow to red as compared with the first embodiment.

In the present embodiment, since orange laser light having a wavelength of 590 nm is used in addition to all the laser light used in the first embodiment, all of the observation modes of the first embodiment and (6) one-substance observation mode (crystal violet emphasis mode) can be performed. Furthermore, in the present embodiment, several observation modes mentioned below can be added.

In the present embodiment, in addition to the two-substance observation mode (hemoglobin-indigo carmine emphasis mode) described in the first embodiment, (7) the two-substance observation mode (hemoglobin-crystal violet emphasis mode) and (8) the two-substance observation mode (indigo carmine-crystal violet emphasis mode) can be performed.

In (7) the two-substance observation mode (hemoglobin-crystal violet emphasis mode), the laser light source LD1 (405 nm), the laser light source LD3 (525 nm), and the laser light source LD5 (590 nm) are turned on at the same time. The light quantity ratio is, for example, 2:1:2. This is because the relationship of the light quantity ratio between the laser light source LD1 and the laser light source LD3 having high absorption intensities of hemoglobin is set to 2:1, which is the ratio of emphasis on the superficial blood vessels, and the light quantity ratio of the light emitted from the laser light source LD1 and the light emitted from the laser light source LD5 is set to 1:1 (=2:2) so that the illumination light quantity of the B pixel range and the illumination light quantity of the R pixel range of the image sensor are substantially equal.

In this manner, it is possible to obtain an emphasized image emphasizing both hemoglobin and crystal violet, and it is possible to support appropriate examination based on the region of presence and pattern, etc., of the two characteristic substances.

In (8) two-substance observation mode (indigo carmine-crystal violet emphasis mode), the laser light source LD4 (635 nm) and the laser light source LD 5 (590 nm) are turned on at the same time. The light quantity ratio is, for example, 1:1. This is to cause the degree of emphasis of contrast between indigo carmine and crystal violet to be equal.

Since both the laser light source LD4 (635 nm) and the laser light source LD5 (590 nm) are included in the red range, if images formed by the light of these two wavelengths are displayed as it is as a red image for the display image, it may be difficult to distinguish the existence patterns of the two characteristic substances. In such case, for example, it is also preferable to display the image formed by the laser light source LD4 (635 nm) in red, and the image formed by the laser light source LD5 (590 nm) in green, so that they are displayed in a color different from the color of the actual characteristic substance. As a result, emphasized images of the two characteristic substances can be distinguished by color and displayed simultaneously.

The light quantity ratio of the illumination light in each mode is not limited to the above ratio. In the case where the light receiving sensitivities of the image sensors in each of the RGB color ranges are different from each other, it is also preferable to adjust the light quantity ratio in consideration of this. Furthermore, in order to alleviate a sense of discomfort for an operator, it is also preferable to adjust the light quantity ratio so that the illumination light comes close to white light.

Furthermore, in the present embodiment, (9) three-substance observation mode (hemoglobin-indigo carmine-crystal violet emphasis mode) is also possible. In this observation mode, the four colors of the laser light source LD1 (emission wavelength 405 nm), the laser light source LD3 (emission wavelength 525 nm), the laser light source LD5 (emission wavelength 590 nm), and the laser light source LD4 (emission wavelength 635 nm) are turned on at the same time. This allows displaying the three characteristic substances of hemoglobin, indigo carmine, and crystal violet with good contrast, so that the operator can examine and evaluate the lesion, etc., based on more information. At this time, by displaying the three characteristic substances in different colors, such as hemoglobin in blue, indigo carmine in red, and crystal violet in green, the three characteristic substances can be displayed in different colors, which allows the operator to easily diagnose.

The light quantity ratio in the three-substance observation mode sets the laser light source LD1 (405 nm), the laser light source LD2 (525 nm), the laser light source LD5 (590 nm), and the laser light source LD4 (635 nm) to 2:1:2:2. This is as a result of setting the light quantity ratio of the blood vessel emphasized by hemoglobin to 2:1, which emphasizes superficial blood vessels, and adjusting the light quantity ratio of indigo carmine and crystal violet to the light quantity of the surface layer of hemoglobin.

Here, although the difference between the three-substance observation mode and the white mode is that whether or not the laser of the laser light source LD2 (445 nm) is turned on among the type of the laser light sources LD1 to LD5 to be turned on, the light quantity ratio is different. In the white observation mode, it is preferable to set a white balance at the start of use or at an appropriate timing so that the light quantity ratio is suitable for white observation. Here, the white balance can be adjusted only by the light quantity ratio of the laser light sources LD1 to LD5, or in combination with general image processing, or by performing only the image processing. In contrast, in the three-substance observation mode, it is preferable to maintain the light quantity ratio at the set value. This is because, if the light quantity ratio is adjusted, the degree of emphasis of each characteristic substance changes, which makes it difficult to determine whether the amount, etc., of the characteristic substance included in the observation object 190 is changed, or the light quantity ratio is different. However, it is preferable to allow operators and maintenance personnel, etc., to adjust the light quantity ratio in the three-substance observation mode according to preference. It is also preferable to display the light quantity ratio for each characteristic substance on a monitor, etc., to notify the operator. This allows the operator to learn which characteristic substance is an illumination emphasized to what extent, eliminating concerns of misunderstanding the emphasis degree of each characteristic substance.

Whether the light quantity ratio can be changed or not, the display thereof, and the method of notifying the operator, etc., as mentioned above are not limited to the three-substance observation mode. In the case of using light having wavelengths in the two-substance observation mode or the one-substance observation mode, or at the time of compound observation with the white observation mode, or in the case of performing overlapped display or parallel display by image processing, it is preferable to inform the operator of the light quantity ratio and the ratio of the degree of emphasis based thereon by numerical values and graphs, etc.

In the present embodiment, the display mode and the characteristic substance extractor are basically the same as those in the first embodiment. Since it is also possible to display an emphasized image of crystal violet in the display mode, it is also preferable to display emphasized images of three characteristic substances, or four or more images including therein an image in white observation mode, in parallel. It is also preferable that the characteristic substance extractor extracts a characteristic substance overlapping range for two desired characteristic substances out of three kinds of characteristic substances of hemoglobin, indigo carmine, and crystal violet. It is also preferable to extract overlapping ranges of three characteristic substances using all three characteristic substances.

By the configuration mentioned above, in addition to the function of the first embodiment, crystal violet can also be observed with good contrast, which allows an image even after the application of crystal violet to be close to an image obtained before the application of crystal violet. Furthermore, these images can be related to the observation mode and the display mode of the first embodiment, and displayed in combination. As a result, the operator will be able to compare and consider even more information as compared with the case of the first embodiment, and use the information for diagnosis and medical evaluation.

Third Embodiment

A third embodiment of the present invention will be described with reference to the drawings. Explanations will be given for the portions different from the first embodiment and the second embodiment, and will be omitted for the same portions.

In the present embodiment, the configuration of a light source unit 132 is different from that of the first embodiment; therefore, an illumination controller 136 and an image processing circuit 156, and information stored in a memory 137 are different from those in the first embodiment.

In the present embodiment, the light source unit 132 includes laser light sources LD6, LD7, and LD8, instead of the laser light source LD3 of the first embodiment. That is, the light source unit 132 includes laser light sources LD1, LD2, LD4, LD6, LD7, and LD8. The characteristics of these laser light sources are as follows.

The laser light source LD1 is configured to emit blue-violet laser light having a wavelength of 405 nm. The output is approximately 1.5 W.

The laser light source LD2 is configured to emit blue laser light having a wavelength of 445 nm. The output is approximately 3 W.

The laser light source LD6 is configured to emit green laser light having a wavelength of 520 nm. The output is approximately 3 W.

The laser light source LD7 is configured to emit bright green laser light having a wavelength of 532 nm. The output is approximately 3 W.

The laser light source LD4 is configured to emit red laser light having a wavelength of 635 nm. The output is approximately 3 W.

The laser light source LD8 is configured to emit deep red laser beam having a wavelength of 680 nm. The output is approximately 3 W.

Each of these laser light sources includes a semiconductor laser element that directly emits laser light of a desired wavelength.

Figure 21:
FIG. 21 shows a spectrum of light that can be emitted by the light source unit in a third embodiment.

FIG. 21 shows a spectrum of light that the light source unit 132 is capable of emitting in the third embodiment. As shown in FIG. 21, in the present embodiment, two wavelengths (laser light source LD1 and laser light source LD2) are allocated to a blue range (400 to 480 nm), two wavelengths (laser light source LD6 and laser light source LD7) are allocated to a green range (480 to 580 nm), and two wavelengths (laser light source LD4 and laser light source LD8) are allocated to a red range (580 to 700 nm).

In this embodiment, in addition to hemoglobin and indigo carmine, Lugol's solution (iodine-potassium iodide solution) is assumed as a characteristic substance. Dye endoscopic observation using Lugol's solution is a diagnostic method using glycogen-iodine coloring reaction, and is used for diagnosis of esophageal cancer (squamous cell carcinoma), etc. When Lugol's solution is applied, the entire mucous membrane is dyed brown. However, in esophageal cancer and esophageal dysplasia (benign malignant border lesion), since glycogen is significantly reduced or disappeared, they are observed as a white state, which is an undyed zone (undyed state). Using this, attention is paid to the undyed zone, and diagnosis is made by biopsy, etc., of such portion.

<Observation Mode>

The observation mode in the present embodiment is different from the first embodiment in that a one-substance observation mode (Lugol's solution emphasis mode) is added in addition to the observation modes described in the first embodiment. The one-substance observation mode (Lugol's solution emphasis mode) will be described.

(9) One-Substance Observation Mode (Lugol's Solution Emphasis Mode)

The present observation mode is an observation mode using illumination light having a wavelength matching the absorption characteristic of Lugol's solution, in order to observe the range dyed with Lugol's solution on the inner surface of the observation object 190 with good contrast so as to be distinguished from the undyed zone.

Lugol's solution is a kind of dye solution that shows a brown color, and has a characteristic of dyeing normal mucous membranes and of not dyeing lesions. In other words, indigo carmine and crystal violet described in the first embodiment and the second embodiment are used for diagnosis and evaluation based on patterns obtained by the accumulation in concave portions or by dyeing of the lesions. On the other hand, Lugol's solution is different in that it has an effect of dyeing portions other than a lesion and causing the lesion to emerge as an undyed zone.

Figure 22:
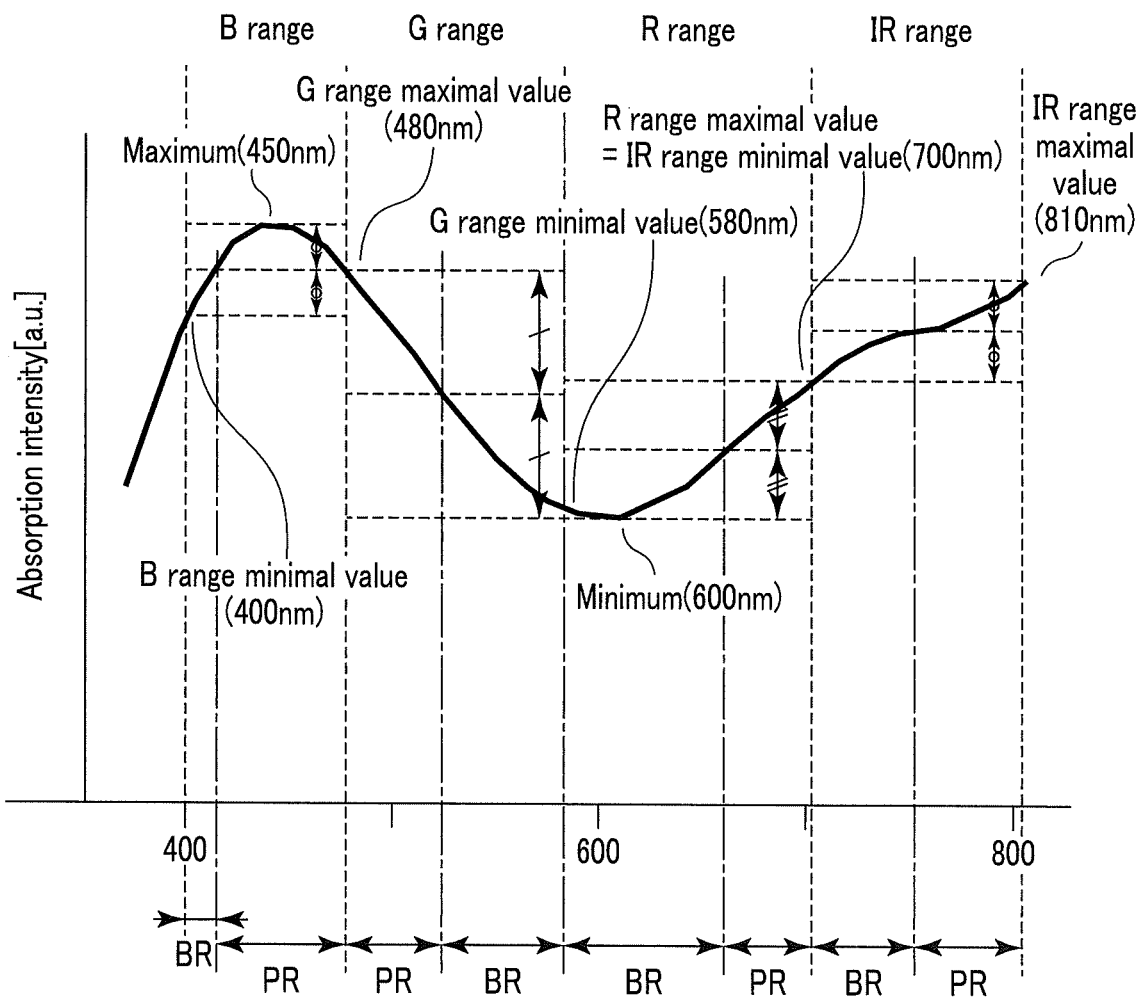
FIG. 22 shows an absorption spectrum of Lugol's solution.

An absorption spectrum of Lugol's solution has light absorption characteristics as shown in FIG. 22. As in the first embodiment and the second embodiment described above, in the absorption spectrum of the Lugol's solution, an intermediate value between a maximal value and a minimal value of a light absorption intensity is set as a threshold value, and a wavelength range having a light absorption intensity higher than the threshold value is set as an absorption peak range PR, and a wavelength range having a light absorption intensity lower than the threshold value is set as an absorption bottom range BR.

As mentioned above, Lugol's solution dyes normal cells, and does not dye lesions. Since the light in the wavelength range of the absorption peak range PR is absorbed in the range dyed with the Lugol's solution, but is not absorbed in the undyed range, the contrast of these two ranges can be improved over that of the white observation mode. On the other hand, since the light in the wavelength range of the absorption bottom range BR is hardly absorbed even in the range dyed with the Lugol's solution, the contrast between the dyed range and the undyed range can be made lower than in the case of the white observation mode. That is, even after application of Lugol's solution, an image with a contrast close to that before the application of Lugol's solution can be obtained.

From FIG. 22, the absorption peak range PR and the absorption bottom range BR of Lugol's solution are as follows.

In a B range, the absorption peak range PR is a wavelength range from 400 to 420 nm and the absorption bottom range BR is a wavelength range from 420 to 480 nm.

In a G range, the absorption peak range PR is a wavelength range from 480 to 525 mn, and the absorption bottom range BR is a wavelength range from 525 to 580 nm.

In an R range, the absorption peak range PR is a wavelength range from 670 to 700 nm, and the absorption bottom range BR is a wavelength range from 580 to 670 nm.

In an IR range, the absorption peak range PR is a wavelength range from 750 to (810) nm, and the absorption bottom range BR is a wavelength range from 700 to 750 nm.

Therefore, in the present embodiment, an emission wavelength (445 nm) of the laser light source LD2, an emission wavelength (520 nm) of the laser light source LD6, and an emission wavelength of the laser light source LD8 (680 nm) are included in the absorption peak range PR, and an emission wavelength (405 nm) of the laser light source LD1, an emission wavelength (532 nm) of the laser light source LD7, and an emission wavelength (680 nm) of the laser light source LD8 are included in the absorption bottom range BR.

Figure 23:
FIG. 23 shows a spectrum of illumination light in the one-substance observation mode (Lugol's solution emphasis mode).

FIG. 23 shows the spectrum of the illumination light in the one-substance observation mode (Lugol's solution emphasis mode). As shown in FIG. 23, in the one-substance observation mode (Lugol's solution emphasis mode), the laser light source LD2 (445 nm), the laser light source LD6 (520 nm), and the laser light source LD8 (680 nm) among the laser light sources LD1, LD2, LD4, LD6, LD7, and LD8 are turned on. As a result, it is possible to observe an undyed zone, which is an undyed range, with a good contrast with respect to the range dyed with Lugol's solution. Laser light having a wavelength of 445 nm, laser light having a wavelength of 520 nm, and laser light having a wavelength of 680 nm are narrow band light selected based on the absorption spectrum of Lugol.

Since the wavelength (520 nm) of the light emitted from the laser light source LD6 among the wavelengths of the laser light used for this one-substance observation mode (Lugol's solution emphasis mode) is also included in the absorption peak wavelength PR of hemoglobin, hemoglobin can be highlighted. Therefore, in the present observation mode, not only can the normal mucous membrane dyed with Lugol's solution look dark, and the undyed zone not dyed with Lugol's solution look bright, but blood vessels where the undyed zone exists can also be highlighted. Thus, it is possible to provide an image that allows the operator to easily perform diagnosis and evaluation. As described above, even in the case where the wavelength is included in the absorption peak range PR of a certain characteristic substance and is also included in the absorption peak range PR of another characteristic substance, if the ranges in which the respective characteristic substances exist are different, it is preferable to use light having such wavelength.

Also in the present observation mode, in the same manner as in the first embodiment and the second embodiment, it is a matter that can be selected as appropriate whether to perform continuous emission, or to turn off the emission during a readout period of the image sensor, etc.

(10) One-Substance Observation Mode (Lugol's Solution Influence Reduction Mode)

A one-substance observation mode (Lugol's solution influence reduction mode), which is an observation mode in which the contrast of Lugol's solution is low, that is peculiar to the present embodiment, will be described. This is a mode that selects only light included in the absorption bottom range BR of Lugol's solution as the illumination light to keep the absorption of the Lugol's solution low, and to enable an image close to that before application of Lugol's solution to be observed.

Figure 24:
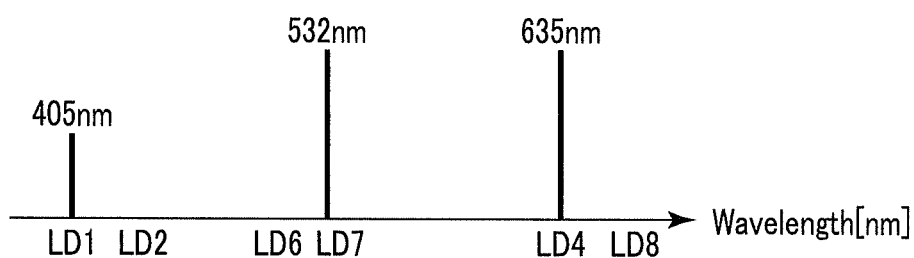
FIG. 24 shows a spectrum of the illumination light in the one-substance observation mode (Lugol's solution influence reduction mode).

FIG. 24 shows the spectrum of the illumination light in the one-substance observation mode (Lugol's solution influence reduction mode). As shown in FIG. 24, in the one-substance observation mode (Lugol's solution influence reduction mode), the laser light source LD1 (405 nm), the laser light source LD7 (532 nm), and the laser light source LD4 (635 nm) among the laser light sources LD1, LD2, LD4, LD6, LD7, and LD8 are turned on. The wavelengths of the laser light included in the illumination light are all included in the absorption bottom range BR of the Lugol's solution. In addition, these three wavelengths are included in three color ranges of RGB, respectively. That is, this illumination light allows obtaining a white image in which the influence of Lugol's solution is reduced as compared with a normal white image even after the application of Lugol's solution. Laser light having a wavelength of 405 nm, laser light having a wavelength of 532 nm, and laser light having a wavelength 635 nm are narrow band light selected based on the absorption spectrum of Lugol.

Therefore, in the present embodiment, it is possible to perform observation practically in two white modes, which are (1) white observation mode that is conducted by illumination light including laser light of six wavelengths as a bright white color mode with high color rendering property, and (10) one-substance observation mode (Lugol's solution influence reduction mode) that enables white observation while reducing the influence of Lugol's solution.

In the present embodiment, by selecting wavelengths in which light is to be emitted based on the absorption peak range PR and the absorption bottom range BR of hemoglobin and indigo carmine described so far, various observation modes and display modes described in the first embodiment and its modifications can be realized.

According to the present embodiment, light source technology and an endoscope apparatus to support diagnosis and evaluation of an operator can be provided by improving the visibility of an abnormal range depending on presence/absence of Lugol's solution, and, simultaneously, improving the contrast of defects in the abnormal range. In addition, even after application of a dye solution, such as Lugol's solution, it is possible to provide a white image with reduced influence thereof.

By using all of the laser light of eight wavelengths used in the first to third embodiments described above, all the observation modes and display modes described above can be obtained. In addition, a four-substance observation mode, and a white observation mode with improved color rendering properties, etc., can be obtained. Furthermore, white observation modes also can be obtained in consideration of the influence of the characteristic substance and the color of the living body.

In all of the embodiments described above, laser light sources are used for the light source unit 132; however, the present invention is not limited thereto. For example, various light sources such as super luminescent diodes, LEDs, and other light sources capable of emitting narrow band light can be used for the light source unit 132. In addition, it is not necessary that all light sources be limited to semiconductor laser elements and LEDs, and they may also be used in combination.

For example, instead of including the laser light source, the light source unit 132 may include LED light sources. FIG. 25 shows the spectrum of the light emitted from the light source unit 132 in which the laser light sources LD1 to LD4 of the first embodiment are replaced by the LED light sources LED1 to LED4. Each of the LED light sources LED1 to LED4 includes an LED element. LED elements are comparatively inexpensive and have a merit such as low risk to the human body.

As shown in FIG. 25, the light emitted by the LED element has a slightly wider spectral width as compared with the semiconductor laser element, but is a sufficiently narrow band light compared with the wavelength range of visible light. Therefore, also in the endoscope apparatus in which the light source unit 132 is configured by the LED light sources LED 1 to LED 4, the same effect as the above embodiments can be obtained.

The criterion for determining whether the wavelength of the light emitted from the LED element is included in the absorption peak range PR or the absorption bottom range BR can be defined by the peak wavelength of the light emitted from the LED element. That is, in the case where the peak wavelength is included in the absorption peak range PR, even if the base of the spectrum deviates from the absorption peak range PR, it is included in the absorption peak range PR. This is because if the peak wavelength is included in the absorption peak range PR, a light quantity exceeding half of the light emitted from the LED is included in the absorption peak range PR. In the above example, the determination is made based on the peak wavelength of the light emitted from the LED. However, it is also possible to use definitions of wavelengths of commonly used LEDs, such as a dominant wavelength.

In addition, it is also possible to produce narrow band light by combining a broad white light source, such as a xenon lamp, and a wavelength filter. According to such combination, it is possible to produce various kinds of narrow band light by filters. In the case of using a filter, as long as it is a wavelength range in which the spectrum of the original illumination light (the emission light of the Xe lamp in this example) exists, it can be cut out as appropriate to configure narrow band light.

For example, the light source unit 132 may be configured to produce narrow band light by a combination of a Xe lamp and filters. FIG. 26 shows spectra of the narrow band light NB1, NB2, NB3, and NB4 produced by a combination of the Xe lamp and the filters. In this example, the narrow band light NB1 and NB3 have wavelength widths covering the entire range of the hemoglobin absorption peak range PR. In addition, the narrow band light NB2 has a wavelength width that matches to a blue range in the hemoglobin absorption bottom range BR. Furthermore, the narrow band light NB4 has a wavelength width that matches to a red range in the indigo carmine absorption peak range PR. Even by using such narrow band light NB1 to NB4, an image that is comparatively bright and high in color reproducibility, in which two characteristic substances are emphasized, can be obtained.

Although the above embodiments have been described assuming that a common observation mode is used in both cases of moving images and still images without distinguishing them in particular, and each observation mode has been described assuming that moving images are acquired, the assumptions are not limited thereto. It is also preferable to set different observation modes for the moving image and the still image. For example, in the case of a still image, it is also preferable to set (5) illumination light sequential radiation mode at all times, to be able to construct an image in a desired observation mode in a later diagnosis or explanation to a patient.

The above-described embodiments are merely examples to which various modifications can be applied without departing from the gist of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope apparatus comprising:
a light source configured to emit at least two kinds of narrow band light including first narrow band light having a wavelength corresponding to an absorption spectrum of a first characteristic substance, and second narrow band light having a wavelength corresponding to an absorption spectrum of a second characteristic substance,
wherein the first narrow band light is included in a color range of one of an R range, a G range, and a B range, and
wherein the second narrow band light is included in a color range of another one of the R range, the G range and the B range that is different from that of the first narrow band light;
a processor configured to control operation of the light source, wherein in controlling operation of the light source, the processor is configured to:
receive an input for selecting a desired observation mode from a one-substance observation mode to control the light source to emit one of the first narrow band light and the second narrow band light selectively to perform observation of only one of the first characteristic substance and the second characteristic substance, and a two-substance observation mode to control the light source to emit the first narrow band light and the second narrow band light simultaneously to perform observation of both the first characteristic substance and the second characteristic substance;
select one of the one-substance observation mode to perform observation of only one of the first characteristic substance and the second characteristic substance, and the two-substance observation mode to perform observation of both the first characteristic substance and the second characteristic substance based on the input received; and
switch between the one-substance observation mode and the two-substance observation mode based on the one-substance observation mode and the two-substance observation mode selected; and
a memory configured to store illumination light control information comprising a wavelength of narrow band light emitted in each of the one-substance observation mode and the two-substance observation mode, a light quantity ratio of each wavelength, and an emission timing, and/or image processing information including an image parameter set in advance with respect to each of the one-substance observation mode and the two-substance observation mode,
wherein the processor is configured to:
read out necessary illumination light control information and/or image processing information from the memory based on the desired observation mode selected; and
operate based on the necessary illumination light control information and/or image processing information.

2. The endoscope apparatus according to claim 1, further comprising:
an insertion section configured to be inserted into an internal space of an observation object;
an image sensor provided at a distal end of the insertion section;
wherein the processor is configured to:
process image information acquired by the image sensor; and
control a display to display the image information processed.

3. The endoscope apparatus according to claim 2,
wherein the image sensor is configured to be controlled by the processor to:
separately acquire first narrow band light image information that is image information acquired by the first narrow band light, and second narrow band light image information that is image information acquired by the second narrow band light, respectively; and
transmit them to the processor, wherein the processor is configured to:
process the first narrow band light image information and the second narrow band light image information, respectively; and
control the display to display at least one of the first narrow band light image and the second narrow band light image.

4. The endoscope apparatus according to claim 3,
wherein the image sensor is configured to separately sense the first narrow band light image and the second narrow band light image,
wherein the image sensor comprises a first color pixel having a first color filter whose transmittance of the first narrow band light is higher than the transmittance of the second narrow band light, and a second color pixel having a second color filter whose transmittance of the second narrow band light is higher than the transmittance of the first narrow band light, and
wherein the image sensor is configured to:
acquire the first narrow band light image with the first color pixel; and
acquire the second narrow band light image with the second color pixel.

5. The endoscope apparatus according to claim 4,
wherein the image sensor comprises a primary color filter type image sensor having a color filter configured to separately sense light of at least three color ranges of the R range, the G range, and the B range, and
wherein, when a color pixel configured to separately acquire light of the R range is defined as an R pixel, a color pixel configured to separately acquire light of the G range is defined as a G pixel, and a color pixel configured to separately acquire light of the B range is defined as a B pixel, the image sensor is configured to separately acquire the first narrow band light image information and the second narrow band light image information with mutually different color pixels.

6. The endoscope apparatus according to claim 4,
wherein the image sensor comprises a complementary color filter type image sensor having a color filter configured to separately sense light of at least three color ranges of an M (Magenta) range, a C (Cyan) range, and a Y (Yellow) range, and
wherein, when a color pixel configured to separately acquire light of the M range is defined as an M pixel, a color pixel configured to separately acquire light of the C range is defined as a C pixel, and a color pixel configured to separately acquire light of the Y range is defined as a Y pixel, the processor is configured to perform image processing that separately acquires the first narrow band light image information and the second narrow band light image information based on image information acquired by the M pixel, the C pixel, and the Y pixel.

7. The endoscope apparatus according to claim 3,
wherein the image sensor comprises a monochrome type image sensor configured to sense light of an entire visible range,
wherein the processor is configured to control the light source to emit the first narrow band light and the second narrow band light at different timings, and
wherein the image sensor is configured to separately acquire the first narrow band light image information and the second narrow band light image information by acquiring the first narrow band light image information and the second narrow band light image information respectively at different timings.

8. The endoscope apparatus according to claim 3,
wherein the light source is configured to emit third narrow band light having a wavelength corresponding to an absorption spectrum of a third characteristic substance, in addition to the first narrow band light and the second narrow band light, the third narrow band light being included in a color range of the other one of the R range, the G range, and the B range that is different from that of the first narrow band light and that of the second narrow band light,
wherein the image sensor is configured to acquire third narrow band light image information, as image information of the third narrow band light, separately from the first narrow band light image information and the second narrow band light image information, and
wherein the processor is configured to:
process the third narrow band light image information independently from the first narrow band light image information and the second narrow band light image information; and
control the display to display the third narrow band light image.

9. The endoscope apparatus according to claim 8,
wherein the endoscope apparatus is configured to perform observation by three one-substance observation modes, three two-substance observation modes, and one three-substance observation mode, and
wherein the processor is configured to control the light source so that:
in the one-substance observation mode, the light source selectively emits one kind of narrow band light that is selected based on a corresponding characteristic substance;
in the two-substance observation mode, the light source selectively emits two kinds of narrow band light that are selected based on each of two corresponding characteristic substances; and,
in the three-substance observation mode, the light source selectively emits three kinds of narrow band light that are selected based on each of three corresponding characteristic substances.

10. The endoscope apparatus according to claim 2,
wherein the one-substance observation mode comprises two modes of a first one-substance observation mode for observing the first characteristic substance and a second one-substance observation mode for observing the second characteristic substance, and
wherein the processor is configured to control emission timings of the first narrow band light and the second narrow band light based on a wavelength relationship between the first narrow band light and the second narrow band light and spectral characteristics of the image sensor so that an image regarding the first characteristic substance and an image regarding the second characteristic substance obtained by the processor processing image information obtained in the two-substance observation mode are equivalent to image information obtained in the first one-substance observation mode and the image information obtained in the second one-substance observation mode, respectively.

11. The endoscope apparatus according to claim 2,
wherein the endoscope apparatus is configured to perform observation according to an illumination light sequential radiation mode, in which:
the light source is configured to sequentially emit plural kinds of narrow band light including at least two kinds of narrow band light included in each of the first narrow band light and the second narrow band light;

the image sensor is configured to independently acquire image information by the plural kinds of narrow band light in sequence; and the processor is configured to construct an image using the image information acquired in sequence, and wherein, in the illumination light sequential radiation mode, the image information by the plural kinds of narrow band light is independently acquired in sequence by setting each of the emission timings of the plural kinds of narrow band light based on a wavelength relationship of the plural kinds of narrow band light emitted from the light source and spectral characteristics of the image sensor.

12. The endoscope apparatus according to claim 1, wherein the light source is configured to emit the illumination light whose spectrum is different in each observation mode.

13. The endoscope apparatus according to claim 12, wherein the one-substance observation mode comprises two modes of a first one-substance observation mode for observing the first characteristic substance and a second one-substance observation mode for observing the second characteristic substance, and wherein the processor is configured to control the light source to emit the first narrow band light in the first one-substance observation mode and emit the second narrow band light in the second one-substance observation mode.

14. The endoscope apparatus according to claim 12, wherein, when, in the absorption spectrum of each characteristic substance, a range having an absorption larger than a first reference value is defined as an absorption peak range, and a range having an absorption smaller than a second reference value that is equal to or smaller than the first reference value is defined as an absorption bottom range, and a visible light range is divided into three color ranges of the R range, the G range, and the B range, the first reference value and the second reference value are set for each of the three color ranges of the R range, the G range, and the B range based on a maximal value and a minimal value for each of the three color ranges of the R range, the G range, and the B range of the absorption spectrum of each characteristic substance, the first narrow band light is included in the absorption peak range of the absorption spectrum of the first characteristic substance, and the second narrow band light is included in the absorption peak range of the absorption spectrum of the second characteristic substance.

15. The endoscope apparatus according to claim 14, wherein the first reference value set for each of the three color ranges is an intermediate value between the maximal value and the minimal value of each color range of the absorption spectrum of each characteristic substance, and wherein the second reference value set for each of the three color ranges is an intermediate value between the maximal value and the minimal value of each color range of the absorption spectrum of each characteristic substance.

16. The endoscope apparatus according to claim 1, wherein the processor is configured to control the light source so that, in the one-substance observation mode, the light source emits plural kinds of narrow band light, each at least included in each of the three color ranges of the R range, the G range, and the B range, the plural kinds of narrow band light including the first narrow band light and the second narrow band light.

17. The endoscope apparatus according to claim 1, wherein the processor is configured to receive an input for selecting a desired display mode from a plurality of display modes.

18. The endoscope apparatus according to claim 17, wherein the plurality of display modes comprise:
an image number selection mode that selects the number of images to be simultaneously displayed on a display; and
an image type selection mode that selects a type of image acquired in each of the one-substance observation mode and the two-substance observation mode to be displayed on the display, and wherein the image type selection mode includes a direct display sub mode that directly displays an image set and displayed for each of the one-substance observation mode and the two-substance observation mode, and an image processing display sub mode that allows a desired image type to be displayed by performing predetermined image processing based on image information obtained by a used observation mode, the processor being configured to switch image processing between the direct display sub mode and the image processing display sub mode.

19. The endoscope apparatus according to claim 1, wherein the light source comprises semiconductor light sources, each of the semiconductor light sources comprising a narrow band semiconductor light source configured to directly emit desired narrow band light.

20. The endoscope apparatus according to claim 19, wherein the narrow band semiconductor light source comprises a semiconductor laser light source configured to emit laser light.

21. The endoscope apparatus according to claim 1, wherein, when one of the first characteristic substance and the second characteristic substance is regarded as a target characteristic substance in the two-substance observation mode, the processor is configured to control the light source to increase a quantity of one of the first narrow band light and the second narrow band light having the wavelength corresponding to the absorption spectrum of the target characteristic substance relative to a quantity of the other of first narrow band light and the second narrow band light.

22. The endoscope apparatus according to claim 1, wherein the first characteristic substance comprises a substance derived from an observation substance contained in an observation object, and wherein the second characteristic substance comprises an externally derived substance that is sprayed, administered, or applied to the observation object.

* * * * *